US012760064B2

(12) United States Patent
Coolbaugh et al.

(10) Patent No.: US 12,760,064 B2
(45) Date of Patent: Oct. 13, 2026

(54) CONTINUOUS PRODUCTION OF RECOMBINANT PROTEINS

(71) Applicant: Genzyme Corporation, Cambridge, MA (US)

(72) Inventors: Michael Coolbaugh, Waltham, MA (US); Tarl Vetter, Framingham, MA (US); Chad Varner, Marlborough, MA (US); Kevin Brower, Holliston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/416,145

(22) Filed: Jan. 18, 2024

(65) Prior Publication Data

US 2024/0150395 A1 May 9, 2024

Related U.S. Application Data

(62) Division of application No. 16/837,126, filed on Apr. 1, 2020, now Pat. No. 11,912,741.

(Continued)

(51) Int. Cl.
*C07K 1/36* (2006.01)
*C12M 1/12* (2006.01)
*C12M 1/26* (2006.01)

(52) U.S. Cl.
CPC ............... *C07K 1/36* (2013.01); *C12M 33/14* (2013.01); *C12M 37/02* (2013.01)

(58) Field of Classification Search
CPC ........... B01D 15/1807; B01D 15/1864; B01D 2311/26; B01D 2311/2688; B01D 2315/08; B01D 2315/16; B01D 61/14; B01D 61/145; B01D 61/58; C07K 1/22; C07K 1/34; C07K 1/36; C07K 16/00; C12M 33/14; C12M 37/02; C12M 47/10; C12P 21/005
See application file for complete search history.

(56) References Cited

U.S. PATENT DOCUMENTS 4,037,984 A 7/1977 Rafferty et al.
4,401,108 A 8/1983 Galkin et al.
(Continued)

FOREIGN PATENT DOCUMENTS

AU 2020202568 B2 6/2022
CN 1146730 A 4/1997
(Continued)

OTHER PUBLICATIONS

Godawat et al., "End-to-end integrated fully continuous production of recombinant monoclonal antibodies", Journal of Biotechnology, 213: 13-9, (Nov. 2015).

(Continued)

*Primary Examiner* — Jennifer Wecker
(74) *Attorney, Agent, or Firm* — Fish & Richardson P.C.

(57) ABSTRACT

The present disclosure relates to methods and systems for the continuous production of recombinant proteins. In particular embodiments, the disclosure relates to methods and systems using capture chromatography, post-capture chromatography, virus filtration, and ultrafiltration/diafiltration for the continuous production of recombinant proteins.

23 Claims, 23 Drawing Sheets

Related U.S. Application Data

(60) Provisional application No. 62/828,755, filed on Apr. 3, 2019.

(56) References Cited

U.S. PATENT DOCUMENTS

| | | | |
|---|---|---|---|
| 4,559,175 | A | 12/1985 | Paciorek et al. |
| 4,599,175 | A | 7/1986 | Yamamizu et al. |
| 4,885,087 | A | 12/1989 | Kopf |
| 4,910,369 | A | 3/1990 | Rich |
| 5,030,346 | A | 7/1991 | McEwen |
| 5,033,943 | A | 7/1991 | Durrum et al. |
| 5,169,936 | A | 12/1992 | Staples et al. |
| 5,360,972 | A | 11/1994 | DiFoggio et al. |
| 5,409,841 | A | 4/1995 | Chow |
| 5,423,982 | A | 6/1995 | Jungbauer et al. |
| 5,458,459 | A | 10/1995 | Hubbard et al. |
| 5,571,720 | A | 11/1996 | Grandics et al. |
| 5,606,033 | A | 2/1997 | Cramer et al. |
| 5,610,285 | A | 3/1997 | Lebing et al. |
| 5,626,767 | A | 5/1997 | Trampler et al. |
| 5,856,179 | A | 1/1999 | Chen et al. |
| 5,985,356 | A | 11/1999 | Schultz et al. |
| 6,022,742 | A | 2/2000 | Kopf |
| 6,085,602 | A | 7/2000 | Schorn et al. |
| 6,127,526 | A | 10/2000 | Blank |
| 6,139,746 | A | 10/2000 | Kopf |
| 6,180,401 | B1 | 1/2001 | Chen et al. |
| 6,265,542 | B1 | 7/2001 | Fahrner et al. |
| 6,296,770 | B1 | 10/2001 | Wilcox et al. |
| 6,307,028 | B1 | 10/2001 | Lebing et al. |
| 6,312,591 | B1 | 11/2001 | Vassarotti et al. |
| 6,333,398 | B1 | 12/2001 | Blank |
| 6,359,114 | B1 | 3/2002 | Grimes et al. |
| 6,365,395 | B1 | 4/2002 | Antoniou |
| 6,375,847 | B1 | 4/2002 | Hartmann |
| 6,410,270 | B1 | 6/2002 | Strittmatter et al. |
| 6,417,335 | B1 | 7/2002 | Basey et al. |
| 6,489,447 | B1 | 12/2002 | Basey et al. |
| 6,544,424 | B1 | 4/2003 | Shevitz |
| 6,544,788 | B2 | 4/2003 | Singh |
| 6,551,512 | B1 | 4/2003 | Britsch et al. |
| 6,586,172 | B1 | 7/2003 | Gunn et al. |
| 6,660,172 | B2 | 12/2003 | Koslow |
| 6,664,095 | B1 | 12/2003 | Suryanarayan et al. |
| 6,870,034 | B2 | 3/2005 | Breece et al. |
| 6,902,909 | B2 | 6/2005 | Navran, Jr. et al. |
| 6,955,917 | B2 | 10/2005 | Alred et al. |
| 7,141,167 | B2 | 11/2006 | Hofmann |
| 7,220,356 | B2 | 5/2007 | Thommes et al. |
| 7,273,554 | B2 | 9/2007 | Rodenberg et al. |
| 7,323,553 | B2 | 1/2008 | Fahrner et al. |
| 7,384,549 | B2 | 6/2008 | de los Reyes et al. |
| 7,510,654 | B2 | 3/2009 | Mir et al. |
| 7,531,645 | B2 | 5/2009 | Basey et al. |
| 7,544,784 | B2 | 6/2009 | Sassenfeld et al. |
| 7,553,938 | B2 | 6/2009 | Buchacher et al. |
| 7,662,930 | B2 | 2/2010 | Zhou |
| 7,673,757 | B2 | 3/2010 | Yavorsky |
| 7,695,627 | B2 | 4/2010 | Bosch et al. |
| 7,695,675 | B2 | 4/2010 | Kaiser et al. |
| 7,714,112 | B2 | 5/2010 | Engstrand et al. |
| 7,759,117 | B2 | 7/2010 | Pham |
| 7,928,205 | B2 | 4/2011 | Dillon et al. |
| 7,988,859 | B2 | 8/2011 | Shinkazh |
| 8,044,017 | B2 | 10/2011 | Emery et al. |
| 8,075,780 | B2 | 12/2011 | Pearce |
| 8,117,924 | B2 | 2/2012 | Joeris |
| 8,119,368 | B2 | 2/2012 | Zijlstra et al. |
| 8,206,981 | B2 | 6/2012 | Crowley et al. |
| 8,222,001 | B2 | 7/2012 | Zijlstra et al. |
| 8,231,788 | B2 | 7/2012 | Mir et al. |
| RE43,655 | E | 9/2012 | Lebing et al. |
| 8,304,231 | B2 | 11/2012 | Roll |
| 8,502,148 | B2 | 8/2013 | Wagner et al. |
| 8,528,225 | B2 | 9/2013 | Weisselberg |
| 8,580,554 | B2 | 11/2013 | Grillberger et al. |
| 9,041,923 | B2 | 5/2015 | Messerchmidt |
| 9,630,165 | B2 | 4/2017 | Godawat et al. |
| 9,650,412 | B2 | 5/2017 | Konstantinov et al. |
| 9,650,413 | B2 | 5/2017 | Konstantinov et al. |
| 9,657,056 | B2 | 5/2017 | Konstantinov et al. |
| 10,071,364 | B2 | 9/2018 | Godawat et al. |
| 10,087,214 | B2 | 10/2018 | Godawat et al. |
| 10,352,770 | B2 | 7/2019 | Morales Rodriguez et al. |
| 10,711,034 | B2 | 7/2020 | Konstantinov et al. |
| 10,919,021 | B2 | 2/2021 | Godawat et al. |
| 10,968,252 | B2 | 4/2021 | Vetter et al. |
| 11,369,703 | B2 | 6/2022 | Patil et al. |
| 11,839,861 | B2 | 12/2023 | Godawat et al. |
| 11,884,703 | B2 | 1/2024 | Vetter et al. |
| 11,912,739 | B2 | 2/2024 | Godawat et al. |
| 11,920,120 | B2 | 3/2024 | Snow |
| 12,073,924 | B2 | 8/2024 | Wasalathanthri et al. |
| 12,110,312 | B2 | 10/2024 | Konstantinov et al. |
| 12,205,680 | B2 | 1/2025 | Wasalathanthri et al. |
| 12,435,305 | B2 | 10/2025 | Snow |
| 2001/0034058 | A1 | 10/2001 | Kopf |
| 2002/0168766 | A1 | 11/2002 | Scapol et al. |
| 2003/0116487 | A1 | 6/2003 | Petersen |
| 2003/0229212 | A1 | 12/2003 | Fahrner et al. |
| 2004/0048330 | A1 | 3/2004 | Bittner |
| 2004/0204379 | A1 | 10/2004 | Cheng et al. |
| 2005/0272146 | A1 | 12/2005 | Hodge et al. |
| 2006/0004621 | A1 | 1/2006 | Malek et al. |
| 2006/0043301 | A1 | 3/2006 | Mantele et al. |
| 2006/0046261 | A1 | 3/2006 | Porter et al. |
| 2006/0051347 | A1 | 3/2006 | Winter |
| 2006/0051874 | A1 | 3/2006 | Reed et al. |
| 2006/0093999 | A1 | 5/2006 | Hei |
| 2006/0183198 | A1 | 8/2006 | Buechler et al. |
| 2007/0131615 | A1 | 6/2007 | Moran et al. |
| 2007/0167612 | A1 | 7/2007 | Hua Zhou |
| 2007/0167613 | A1 | 7/2007 | Johansson et al. |
| 2007/0244307 | A1 | 10/2007 | Engstrand et al. |
| 2007/0249030 | A1 | 10/2007 | Fehrenthold et al. |
| 2008/0017576 | A1 | 1/2008 | Belfort et al. |
| 2008/0031877 | A1 | 2/2008 | Covacci et al. |
| 2008/0132688 | A1 | 6/2008 | Zhou |
| 2008/0207487 | A1 | 8/2008 | DeFrees et al. |
| 2009/0166290 | A1 | 7/2009 | Anderson |
| 2009/0166300 | A1 | 7/2009 | Osborn et al. |
| 2009/0199904 | A1 | 8/2009 | Babbitt et al. |
| 2009/0296075 | A1 | 12/2009 | Hu et al. |
| 2009/0298121 | A1 | 12/2009 | Schwartz et al. |
| 2010/0056645 | A1 | 3/2010 | Deorkar et al. |
| 2010/0081122 | A1 | 4/2010 | Shibuya et al. |
| 2010/0151558 | A1 | 6/2010 | Alianell et al. |
| 2010/0237013 | A1 | 9/2010 | Burke et al. |
| 2010/0255526 | A1 | 10/2010 | Braet et al. |
| 2010/0330627 | A1 | 12/2010 | Shimada et al. |
| 2011/0011486 | A1 | 1/2011 | Pottier et al. |
| 2011/0070602 | A1 | 3/2011 | Thomson et al. |
| 2011/0081672 | A1 | 4/2011 | Andersen et al. |
| 2011/0111486 | A1 | 5/2011 | Furey |
| 2011/0160435 | A1 | 6/2011 | Borgvall et al. |
| 2011/0312087 | A1 | 12/2011 | Khan |
| 2012/0125847 | A1 | 5/2012 | Sehgal |
| 2012/0164066 | A1 | 6/2012 | Greene et al. |
| 2012/0255642 | A1 | 10/2012 | Gebauer |
| 2013/0059371 | A1 | 3/2013 | Shevitz |
| 2013/0061941 | A1 | 3/2013 | Gebauer |
| 2013/0068671 | A1 | 3/2013 | Gebauer et al. |
| 2013/0143313 | A1 | 6/2013 | Niazi |
| 2013/0164796 | A1 | 6/2013 | Licamele et al. |
| 2013/0164824 | A1 | 6/2013 | Licamele et al. |
| 2013/0260419 | A1 | 10/2013 | Ransohoff et al. |
| 2013/0280788 | A1 | 10/2013 | Skudas |
| 2013/0344535 | A1 * | 12/2013 | Mundt .................. C12M 37/02 435/41 |
| 2014/0038264 | A1 | 2/2014 | Grillberger et al. |
| 2014/0120605 | A1 | 5/2014 | Wolters et al. |
| 2014/0123777 | A1 | 5/2014 | Newbold et al. |
| 2014/0154270 | A1 | 6/2014 | Wang et al. |
| 2014/0154726 | A1 | 6/2014 | Yang et al. |

(56) References Cited

U.S. PATENT DOCUMENTS

2014/0255994 A1 9/2014 Konstantinov et al.
2014/0295532 A1 10/2014 Ray et al.
2014/0373606 A1 12/2014 Kraiczek et al.
2015/0158907 A1 6/2015 Zhou et al.
2015/0183821 A1 7/2015 Konstantinov et al.
2015/0202595 A1 7/2015 Godawat et al.
2015/0203529 A1 7/2015 Godawat et al.
2015/0203531 A1 7/2015 Godawat et al.
2015/0203532 A1* 7/2015 Godawat ................ B01D 15/20
435/208
2015/0232505 A1 8/2015 Konstantinov et al.
2015/0274773 A1 10/2015 Becker et al.
2015/0275195 A1 10/2015 Godawat et al.
2015/0299249 A1 10/2015 Herigstad et al.
2015/0345689 A1 12/2015 Selker et al.
2016/0059159 A1* 3/2016 Steen .................. B01D 29/603
210/788
2016/0115438 A1 4/2016 Snow
2016/0325204 A1 11/2016 Peyser et al.
2017/0058308 A1 3/2017 Aakesson et al.
2017/0218012 A1 8/2017 Konstantinov et al.
2018/0051054 A1 2/2018 Vetter et al.
2018/0113025 A1 4/2018 Morales Rodriguez et al.
2018/0154280 A1 6/2018 Peyser et al.
2018/0214587 A1 8/2018 Mao et al.
2018/0339244 A1 11/2018 Hubbuch et al.
2018/0354986 A1 12/2018 Godawat et al.
2018/0369786 A1 12/2018 Godawat et al.
2019/0009215 A1 1/2019 Heise et al.
2019/0112569 A1 4/2019 Czeterko et al.
2019/0272894 A1 9/2019 Wasalathanthri et al.
2020/0069822 A1 3/2020 Patil et al.
2020/0124817 A1 4/2020 Ohmori et al.
2020/0317726 A1 10/2020 Konstantinov et al.
2020/0369718 A1 11/2020 Godawat et al.
2021/0002601 A1 1/2021 Snow
2021/0171572 A1 6/2021 Vetter et al.
2021/0268477 A1 9/2021 Godawat et al.
2021/0269477 A1 9/2021 Konstantinov et al.
2022/0081669 A1 3/2022 Snow
2022/0101953 A1 3/2022 Wasalathanthri et al.
2023/0295224 A1 9/2023 Coolbaugh et al.
2024/0417427 A1 12/2024 Konstantinov et al.
2025/0246268 A1 7/2025 Wasalathanthri et al.
2026/0049100 A1 2/2026 Konstantinov et al.

FOREIGN PATENT DOCUMENTS

CN 1157634 A 8/1997
CN 1807599 A 6/2003
CN 1526732 A 9/2004
CN 1606457 A 4/2005
CN 1713951 A 12/2005
CN 1923290 A 3/2007
CN 101074928 A 11/2007
CN 101182465 A 5/2008
CN 101200691 A 6/2008
CN 101889025 A 11/2010
CN 102257006 A 11/2011
CN 102321316 A 1/2012
CN 102459560 A 5/2012
CN 102655919 A 9/2012
CN 102656452 A 9/2012
CN 102911268 A 2/2013
CN 102947696 A 2/2013
CN 103153334 A 6/2013
CN 103223333 A 7/2013
CN 103562145 A 2/2014
CN 103630515 A 3/2014
CN 203513669 U 4/2014
CN 104406836 A 3/2015
CN 104884467 A 9/2015
CN 105358572 A 2/2016
CN 105377874 A 3/2016
CN 105916561 A 8/2016
CN 106068150 A 11/2016
CN 106715670 A 5/2017
CN 106794424 A 5/2017
CN 107267490 A 10/2017
CN 112206847 A 1/2021
DE 4333560 A1 4/1995
DE 9421778 U1 11/1996
EP 0206433 A2 12/1986
EP 0281368 A2 11/1989
EP 0621074 A1 10/1994
EP 1203774 A1 5/2002
EP 1498475 A1 1/2005
EP 2020433 A2 2/2009
EP 2020433 B1 2/2009
EP 2649016 10/2013
EP 2682168 A1 1/2014
EP 3129460 A1 4/2015
EP 2964663 A2 1/2016
EP 3047013 B1 7/2016
EP 3173782 A1 5/2017
GB 2476580 A 2/2011
JP S60-000804 A 1/1985
JP S61-088872 A 7/1986
JP S63-123377 U 5/1988
JP S63-151306 A 6/1988
JP H04-78426 A 3/1992
JP H05-031335 A 2/1993
JP H05-322747 A 12/1993
JP H07-110229 A 4/1995
JP 4260877 B2 6/1995
JP H08-503615 A 4/1996
JP 2002-262855 A 9/2002
JP 2003-012693 A 1/2003
JP 2005-503239 A 2/2005
JP 2005-140794 A 6/2005
JP 4638153 B2 10/2005
JP 2006-300965 A 11/2006
JP 2008-504845 A 2/2008
JP 2008-512473 A 4/2008
JP 2008-518885 A 6/2008
JP 2008-526203 A 7/2008
JP 4260877 B 4/2009
JP 2009-543565 A 12/2009
JP 2010-011792 A 1/2010
JP 2012-510981 A 5/2012
JP 2012-520078 A 9/2012
JP 2012-521776 A 9/2012
JP 2013-505462 A 2/2013
JP 2013-509216 A 3/2013
JP 2014-182102 A 3/2013
JP 2013-515251 A 5/2013
JP 2013-515258 A 5/2013
JP 2013-527473 A 6/2013
JP 2013-544524 A 12/2013
JP 2017-518749 A 5/2015
JP 2015-533378 A 11/2015
JP 2016-510981 A 4/2016
JP 2016-519137 A 6/2016
JP 2017-508135 A 3/2017
JP 2017-509866 A 4/2017
JP 2017-515501 A 6/2017
JP 2017-522169 A 8/2017
JP 2018-192430 A 1/2018
KR 10-2007-0109975 A 11/2007
KR 10-2009-0105961 A 10/2009
RU 2034853 C1 5/1995
RU 2274471 C2 4/2006
RU 2390526 C2 5/2010
RU 102618 U1 3/2011
RU 109275 U1 10/2011
RU 2713126 C2 2/2020
SU 1033181 A1 8/1983
TW M283863 U 12/2005
TW 201538521 A 10/2015
TW 1553021 B 10/2016
TW 1591782 B 7/2017
TW 1671312 B 9/2019
TW 1691342 B 4/2020

(56) References Cited

FOREIGN PATENT DOCUMENTS

| | | | | |
|---|---|---|---|---|
| WO | 1991/006008 A1 | 5/1991 | | |
| WO | 1992/017403 A1 | 10/1992 | | |
| WO | 1993/017724 A1 | 9/1993 | | |
| WO | 1994/022490 A1 | 10/1994 | | |
| WO | 1996/008556 A1 | 3/1996 | | |
| WO | 1997/017436 A1 | 5/1997 | | |
| WO | 2002/041989 A1 | 5/2002 | | |
| WO | 2003043439 | 5/2003 | | |
| WO | 2003/045546 A1 | 6/2003 | | |
| WO | 2006/021873 A2 | 3/2006 | | |
| WO | 2006/031560 A2 | 3/2006 | | |
| WO | 2006/039533 A2 | 4/2006 | | |
| WO | 2006/039588 A2 | 4/2006 | | |
| WO | 2006/043896 A1 | 4/2006 | | |
| WO | 2006/096116 A1 | 9/2006 | | |
| WO | 2008/006494 A1 | 1/2008 | | |
| WO | 2008/073620 A2 | 6/2008 | | |
| WO | 2008/094237 A1 | 8/2008 | | |
| WO | 2008/110291 A1 | 9/2008 | | |
| WO | 2008/127087 A1 | 10/2008 | | |
| WO | 2008/153472 A1 | 12/2008 | | |
| WO | 2009/008812 A1 | 1/2009 | | |
| WO | 2009/103791 A1 | 8/2009 | | |
| WO | 2010/066734 A1 | 6/2010 | | |
| WO | 2010/112576 A1 | 10/2010 | | |
| WO | 2010/149259 A2 | 12/2010 | | |
| WO | 2011/038008 A2 | 3/2011 | | |
| WO | 2011/051406 A1 | 5/2011 | | |
| WO | 2011/076386 A1 | 6/2011 | | |
| WO | 2011/078772 A1 | 6/2011 | | |
| WO | 2011/147762 A2 | 12/2011 | | |
| WO | 2011/152788 A1 | 12/2011 | | |
| WO | 2012/032354 A1 | 3/2012 | | |
| WO | 2012/073677 A1 | 6/2012 | | |
| WO | 2012/074481 A1 | 6/2012 | | |
| WO | 2012/078677 A2 | 6/2012 | | |
| WO | 2012/128703 A1 | 9/2012 | | |
| WO | 2013/045546 A1 | 4/2013 | | |
| WO | 2013/096682 A1 | 6/2013 | | |
| WO | 2013/109520 A1 | 7/2013 | | |
| WO | 2013/124326 A1 | 8/2013 | | |
| WO | 2013/159858 A1 | 10/2013 | | |
| WO | 2014/004103 A1 | 1/2014 | | |
| WO | 2014/004281 A1 | 1/2014 | | |
| WO | 2014/051503 A1 | 4/2014 | | |
| WO | 2014/067898 A1 | 5/2014 | | |
| WO | 2014/137903 A2 | 9/2014 | | |
| WO | 2014/180852 | 11/2014 | | |
| WO | 2015/039115 A1 | 3/2015 | | |
| WO | 2015198320 | 6/2015 | | |
| WO | 2015/109146 A1 | 7/2015 | | |
| WO | 2015/109151 A1 | 7/2015 | | |
| WO | 2015/109246 A1 | 7/2015 | | |
| WO | 2015/155353 A1 | 10/2015 | | |
| WO | 2015/175679 | 11/2015 | | |
| WO | 2017/088979 A1 | 6/2017 | | |
| WO | 2017/174580 A1 | 10/2017 | | |
| WO | 2018035116 | 2/2018 | | |
| WO | 2018164995 | 3/2018 | | |
| WO | 2018/140887 A1 | 8/2018 | | |
| WO | WO-2020159838 A1 * | 8/2020 | ............ | B01D 71/34 |

OTHER PUBLICATIONS

Konstantinov et al., "White Paper on Continuous Bioprocessing" J. Pharm. Sci. 104(3): 813-20 (Mar. 2015).

Orozco et al., "Design, construction, and optimization of a novel, modular, and scalable incubation chamber for continuous viral inactivation", Biotechnology Progress, 33(4): 954-965, (Jul. 2017).

Parker et al., "Design of a novel continuous flow reactor for low pH viral inactivation", Biotechnology and Bioengineering, 115(3): 606-616, (Mar. 2018).

Steinebach et al., "Design and operation of a continuous integrated monoclonal antibody production process", Biotechnology Press, 33(5): 1303-1313, (Sep. 2017).

The International Search Report and Written Opinion of the International Searching Authority for International Application No. PCT/US2020/026107; mailed Jul. 10, 2020, p. 1-6.

Zydney, "Continuous downstream processing for high value biological products: A Review" Biotechnol. Bioeng_ 113 (3): 465-75 (Mar. 2016).

Bisschops et al., "6. Two Mutually Enabling Trends: Continuous Bioprocessing and Single-Use Technologies"; in: Ganapathy Subramanian: "Continuous Biomanufacturing: Innovative Technologies and Methods", Wiley-VHC, Wenheim, XP009521341, ISBN: 978-3-527-34063-7, pp. 149-169, (2018).

Gracheva. "Technology of Enzyme Preparations". 2nd edition, 1987 in "Textbooks and tutorials for Higher Educational Institutions Students". (Machine translation provided).

Sao Pedro et al. "White paper on high-throughput process development for integrated continuous biomanufacturing" Biotechnol Bioeng. 118(9):3275-86 (2021).

Watertechonline.com [online], "The Simple Backpressure Valve: Workhorse of Water Treatment," May 1, 2007, retrieved on Sep. 3, 2025, retrieved from URL <https://www.watertechonline.com/home/article/14171274/the-simple-backpressure-valve-workhorse-of-water-treatment>, 8 pages.

Waterworld.com [online], "Damaging Flow Phenomena: Destructive Factors Determine Centrifugal Pump Minimum Flow Rates," May 1, 2013, retrieved on Sep. 3, 2025, retrieved from URL <https://www.waterworld.com/wastewater-treatment/article/16190836/damaging-flow-phenomena-destructive-factors-determine-centrifugal-pump-minimum-flow-rates>, 6 pages.

Watson Marlow Bredel Manuals, "Watson-Marlow 620UN/620U, 620SN/620S pumps," Watson Marlow Pumps, Sep. 19, 2005, 100 pages.

Watt, "Automatically Controlled Continuous Recovery of Plasma Protein Fractions for Clinical Use: A Preliminary Report," Vox Sanguinis, Jan. 1970, 18(1): 42-61.

Weaver et al., "Uridine phosphorylase purified from total crude extracts of *E. coli*using Q Sepharose and radial-flow chromatography," BioPharm, 1990, 3(7):25-28.

Wong et al., "Development of Continuous Crystallization Processes Using a Single-Stage Mixed-Suspension, Mixed-Product Removal Crystallizer with Recycle," Crystal Growth & Design, Oct. 2012, 12(11):5701-5707.

Wright et al., "A Novel Seed-Train Process: Using High-Density Cell Banking, a Disposable Bioreactor, and Perfusion Technologies," Bioprocess International, Mar. 2015, 10 pages.

Written Opinion in Singapore Appln. No. 11201901220X, mailed on Oct. 15, 2020, 8 pages.

Written Opinion in Singapore Appln. No. 10201709131U, mailed on Dec. 24, 2021, 6 pages.

Written Opinion in Singapore Appln. No. 10201709131U, mailed on Feb. 11, 2019, 3 pages.

Written Opinion in Singapore Appln. No. 10201709131U, mailed on Jun. 29, 2020, 4 pages.

Written Opinion in Singapore Appln. No. 10201801943S, mailed on Aug. 18, 2023, 9 pages.

Written Opinion in Singapore Appln. No. 10201801943S, mailed on Jun. 22, 2022, 9 pages.

Written Opinion in Singapore Appln. No. 1021804483P, mailed on Sep. 25, 2023, 5 pages.

Written Opinion in Singapore Appln. No. 11201506775V, mailed on Aug. 16, 2016, 6 pages.

Written Opinion in Singapore Appln. No. 11201601899T, mailed on Mar. 1, 2018, 8 pages.

Written Opinion in Singapore Appln. No. 11201601899T, mailed on Mar. 9, 2017, 10 pages.

Written Opinion in Singapore Appln. No. 11201605625X, mailed on May 25, 2017, 8 pages.

Written Opinion in Singapore Appln. No. 11201605626S, mailed on Jul. 23, 2020, 5 pages.

Written Opinion in Singapore Appln. No. 11201605626S, mailed on May 25, 2017, 6 pages.

(56) References Cited

OTHER PUBLICATIONS

Written Opinion in Singapore Appln. No. 11201605626S, mailed on Nov. 15, 2019, 9 pages.
Written Opinion in Singapore Appln. No. 11201605626S, mailed on Sep. 4, 2018, 5 pages.
Written Opinion in Singapore Appln. No. 11201901220X, mailed on Jul. 15, 2022, 5 pages.
Written Opinion in Singapore Appln. No. 11202101860U, mailed on Oct. 7, 2022, 9 pages.
Written Opinion in Singapore Appln. No. 11202101860U, mailed on Sep. 17, 2024, 9 pages.
Written Opinion in Taiwanese Appln. No. 103107864, mailed on Sep. 11, 2018, 10 pages.
Written Opinion in Taiwanese Appln. No. 104101335, mailed on Feb. 11, 2019, 4 pages.
Written Opinion in Taiwanese Appln. No. 104101335, mailed on Jan. 11, 2019, 1 page.
Written Opinion in Taiwanese Appln. No. 108105550, mailed on Feb. 6, 2020, 7 pages.
Xie et al., "Preparative chromatographic separation: Simulated moving bed and modified chromatography methods," Biotechnology and Bioprocess Engineering, Dec 2001, 6(6):363-375.
Xu et al., "High-density mammalian cell cultures in stirred-tank bioreactor without external pH control," Journal of Biotechnology, Aug. 2016, 231:149-159.
Yabannavar et al., "Mammalian cell retention in a spinfilter perfusion bioreactor," Biotechnology and Bioengineering, Oct. 1992, 40(8):925-933.
Yang et al., "Perfusion seed cultures improve biopharmaceutical fed-batch production capacity and product quality," Biotechnology Progress, Feb. 2014, 30(3):616-625.
Zbikowska et al., "Protein modification caused by a high dose of gamma irradiation in cryosterilizedplasma: Protective effects of ascorbate," Free Radical Biology & Medicine, Feb. 2006, 40:536-542.
Zhao et al., "Adsorbents for Expanded Bed Adsorption: Preparation and Functionalization," Chinese Journal of Chemical Engineering, 2009, 17(4):678-687.
Fox et al., "Continuous chromatography apparatus: I. Construction," Journal of Chromatography A, 1969, 43:48-54.
Fox, "Continuous chromatography apparatus: II. Operation," Journal of Chromatography A, 1969, 43:55-60.
Furuta et al., "Continuous crystallization using a sonicated tubular system for controlling particle size in an API manufacturing process," Chemical Engineering and Processing: Process Intensification, Apr. 2016, 102:210-218.
Gagnon et al., "Technology trends in antibody purification," Journal of Chromatography A, Jan. 2012, 1221:57-70.
Gagnon, "Dissection of the Separation Mechanisms and Enhancement of Aggregate Removal by Charged-Hydrophobic Mixed Mode Chromatography," 6th International Symposium on HIC and RPC, 2009, 30 pages.
Gaida et al., "Selective Retention of Viable Cells in Ultrasonic Resonance Field Devices," Biotechnology Progress, 1996, 12(1): 73-76.
GE Healthcare Life Sciences, "Protein A SepharoseTM CL-4B," dated May 2011, 8 Pages.
GE Healthcare, "Capto Adhere - Affinity Chromatography," 2006, 4 pages.
GE Healthcare, "Ion Exchange Chromatography & Chromatofocusing Principles and Methods Ion Exchange Chromatography & Chromatofocusing—Principles and Methods imagination at work," GE Healthcare Bio-Sciences, 2010, 8 pages.
GE Healthcare, "Multimodal Chromatography," Handbook GE Healthcare Life Sciences, Nov. 2013, 7 pages.
GE Healthcare, "Use of sodium hydroxide for cleaning and sanitizing chromatography media and systems," Process Chromatography Application Note 18-1124-57 AF, 2006, pp. 1-8.
Gebauer et al., "Engineered protein scaffolds as next-generation antibody therapeutics," Current Opinion in Chemical Biology, Jun. 2009, 13(3):245-255.
Giddings, "Theory of Minimum Time Operation in Gas Chromatography.," Analytical Chemistry, Mar. 1962, 34 (3):314-319.
Gil et al., "Challenging the Cleanroom Paradigm for Biopharmaceutical Manufacturing of Bulk Drug Substances," BioPharm International, Aug. 1, 2011, 9 pages.
Giovannini et al., "Isolation of a recombinant antibody from cell culture supernatant: Continuous annular versus batch and expanded-bed chromatography," Biotechnology and Bioengeering, Jun. 2001, 73(6): 522-529.
Godawat et al., "Periodic counter-current chromatography - design and operational considerations for integrated and continuous purification of proteins," Biotechnology Journal, Dec 2012, 7(12):1496-1508.
Gomes et al., "Purification of plasmid DNA with aqueous two phase systems of PEG 600 and sodium citrate/ ammonium sulfate," Separation and Purification Technology, Feb. 2009, 65(1):22-30.
Gorenflo et al., "Optimization of an Acoustic Cell Filter with a Novel Air-Backflush System," Biotechnology Progress, Feb. 2003, 19(1):30-36.
Gorenflo et al., "Scale-up and optimization of an acoustic filter for 200 L/day perfusion of a CHO cell culture," Biotechnology and Bioengineering, Sep. 2002, 80(4):438-444.
Gottschlich et al., "Purification of monoclonal antibodies by simulated moving-bed chromatography," Journal of Chromatography A, Mar. 1997, 765(2):201-206.
Grabski et al., "Simulated moving bed chromatography," Genetic Engineering & Biotechnology News [online], Oct. 15, 2009 [retrieved on Jul. 16, 2014]. Retrieved from the Internet: < URL: http://www.genengnews.com/gen-articles/simulated-moving-bed-chromatography/3076/>, 29(18): 4.
Greenfield et al., "Experience in scale-up of homogeneous perfusion culture for hybridomas," Bioprocess Engineering, Jun. 1991, 6(5):213-219.
Grein et al., "Virus Separation Using Membranes," Animal Cell Biotechnology: Methods and Protocols, Methods in Molecular Biology, 2014, 1104: 459-491.
Groot et al., "Process engineering for a membrane recycle fermentor," Bioprocess Engineering, 1993, 8:235-246.
Gruener, "Guide to Irradiation and Sterilization Validation of Single-Use Bioprocess Systems," BioProcess International, May 2008, pp. 10S-22S.
Gu et al., "A theoretical study of multicomponent radial flow chromatography," Chemical Engineering Science, 1991, 46(5): 1279-1288.
Haenlein et al., "A Beginner's Guide to Partial Least Squares Analysis," Understanding Statistics, 2004, 3(4):283-297.
Hamamoto et al., "Perfusion culture of hybridoma cells using a centrifuge to separate cells from culture mixture," Journal of Fermentation and Bioengineering, 1989, 67(3):190-194.
Hammerschmidt et al., "Continuous polyethylene glycol precipitation of recombinant antibodies: Sequential precipitation and resolubilization," Process Biochemistry, Feb. 2016, 51(2):325-332.
Hammerschmidt et al., "Continuous precipitation of lgG from CHO cell culture supernatant in a tubular reactor," Biotechnology Journal, Aug. 2015, 10(8):1196-1205.
Hammerschmidt et al., "Economics of recombinant antibody production processes at various scales: Industry-standard compared to continuous precipitation," Biotechnology Journal, Apr. 2014, 9(6):766-775.
Haraguchi et al., "Phase equilibrium and insulin partitioning in aqueous two-phase systems containing block copolymers and potassium phosphate," Fluid Phase Equilibria, Jan. 2004, 215(1): 1-15.
Hart et al., "Large Scale, In Situ Isolation of Periplasmic IGF-I from *E. coli*," Nature Biotechnology, Nov. 1994, 12 (11):1113-1117.
Hecht et al., "Efficiency improvement of an antibody production process by increasing the inoculum density," Biotechnology Progress, Feb. 2014, 30(3):607-615.
Heeter et al., "Perfusion chromatography: performance of periodic countercurrent col. operation and its comparison with fixed-bed operation," Journal of Chromatography, Sep. 1995, 711(1): 3-21.

(56) References Cited

OTHER PUBLICATIONS

Hekmat, "Large-scale crystallization of proteins for purification and formulation," Bioprocess Biosystems Engineering, Feb. 2015, 38(7):1209-1231.
Himmelfarb et al., "Spin Filter Culture: The Propagation of Mammalian Cells in Suspension," Science, May 1969, 164 (3879):555-557.
Holzer et al., "Multicolumn chromatography: A new approach to relieving capacity bottlenecks for downstream processing efficiency," BioProcess International, Sep. 6, 2008, (8):74-84.
Huang et al., "Mathematical models of radial chromatography". The Chemical Engineering Journal, Jul. 1988, 38 (3):179-186.
Hülscher et al., "Selective recycle of viable animal cells by coupling of airlift reactor and cell settler," Biotechnology and Bioengineering, Feb. 1992, 39(4):442-446.
Imamoglu, "Simulated Moving Bed Chromatography (SMB) for Application in Bioseparation," Modern Advances in Chromatography, May 2002, pp. 211-231.
Interbiotech—BioScience Innovations, "KrosFlo Hollow Fibers Ultra/Filtration Modules," Interchim Innovations, available no later than Sep. 16, 2013, 13 pages.
International Preliminary Report on Patentability in International Appln. No. PCT/US2014/055897, mailed on Mar. 22, 2016, 8 pages.
International Preliminary Report on Patentability in International Appln. No. PCT/US2014/019909, mailed on Sep. 17, 2015, 7 pages.
International Preliminary Report on Patentability in International Appln. No. PCT/US2015/056422, mailed on Apr. 25, 2017, 6 pages.
International Preliminary Report on Patentability in International Appln. No. PCT/US2017/046930, mailed on Feb. 19, 2019, 7 pages.
International Preliminary Report on Patentability in International Appln. No. PCT/US2019/020355, mailed on Sep. 8, 2020, 8 pages.
International Preliminary Report on Patentability in International Appln. No. PCT/US2020/026107, mailed on Oct. 14, 2021, 15 pages.
International Preliminary Report on Patentability in International Appln. No. PCT/US2023/013764, mailed on Oct. 3, 2024, 8 pages.
International Preliminary Report on Patentability in International Appln. No. PCT/US2015/011698, mailed on Jul. 19, 2016, 7 pages.
International Preliminary Report on Patentability in International Appln. No. PCT/US2015/011705, mailed on Jul. 19, 2016, 10 pages.
International Preliminary Report on Patentability in International Appln. No. PCT/US2019/046893, mailed on Mar. 2, 2021, 10 pages.
International Search Report and Written Opinion in International Appln. No. PCT/US2014/019909, mailed on May 21, 2014, 10 pages.
International Search Report and Written Opinion in International Appln. No. PCT/US2014/055897, mailed on Dec. 5, 2014, 12 pages.
International Search Report and Written Opinion in International Appln. No. PCT/US2015/011698, mailed on Apr. 17, 2015, 11 pages.
International Search Report and Written Opinion in International Appln. No. PCT/US2015/011705, mailed on Apr. 30, 2015, 14 pages.
International Search Report and Written Opinion in International Appln. No. PCT/US2015/056422, mailed on Apr. 4, 2016, 11 pages.
International Search Report and Written Opinion in International Appln. No. PCT/US2017/046930, mailed on Oct. 27, 2017, 11 pages.
International Search Report and Written Opinion in International Appln. No. PCT/US2019/020355, mailed on May 24, 2019, 12 pages.
International Search Report and Written Opinion in International Appln. No. PCT/US2019/046893, mailed on Nov. 20, 2019, 12 pages.
International Search Report and Written Opinion in International Appln. No. PCT/US2023/013764, mailed on May 19, 2023, 13 pages.
Invitation to Amend in Singapore Appln. No. 10201803601S, mailed on Jul. 25, 2023, 5 pages.
Ip.com [online] "Method for radiation sterilization of sensitive chromatographic resins and membranes," IP.com No. IPCOM000188023D, Sep. 18, 2009, 2 pages.
Ito et al., "Centrifugal precipitation chromatography," Journal of Chromatography B, Jan. 2010, 878(2):154-164.
Jayapal et al., "Recombinant protein therapeutics from CHO cells-20 years and counting," Chemical engineering progress, Oct. 2007, 103(10):40.
Jen et al., "Review: Hydrogels for cell immobilization," Biotechnology and Bioengineering, May 1996, 50(4):357-364.
Jockwer et al., "The use of hydroclones for mammalian cell retention in perfusion bioreactors," Animal Cell Technology: From Target to Market, 2001, pp. 301-306.
Johnson et al., "Use of the Centritech Lab Centrifuge for Perfusion Culture of Hybridoma Cells in Protein-Free Medium," Biotechnology Progress, 1996, 12(6):855-864.
Jungbauer et al., "Continuous downstream processing of biopharmaceuticals," Trends in Biotechnology, Aug. 2013,31(8):479-492.
Kang et al., "Development of a novel and efficient cell culture flocculation process using a stimulus responsive polymer to streamline antibody purification processes," Biotechnology and Bioengineering, Jun. 2013, 110(11):2928-2937.
Karst et al., "Characterization and comparison of ATF and TFF in stirred bioreactors for continuous mammalian cell culture processes," Biochemical Engineering Journal, Jun. 2016, 110:17-26.
Kawahara et al., "High-density culture of FM-3A cells using a bioreactor with an external tangential-flow filtration device," Cytotechnology, Jan. 1994, 14(1):61-66.
Kebler et al., "Step gradients in 3-zone simulated moving bed chromatography: Application to the purification of antibodies and bone morphogenetic protein-2," Journal of Chromatography A, Dec. 2007, 1176(1):69-78.
Kelly et al., "Understanding and modeling alternating tangential flow filtration for perfusion cell culture," Biotechnology Progress, Nov. 2014, 30(6):1291-1300.
Kilburn et al., "Enhanced sedimentation of mammalian cells following acoustic aggregation," Biotechnology and Bioengineering, Aug. 1989, 34(4):559-562.
Kim et al., "Application of a Cell-Once-Through Perfusion Strategy for Production of Recombinant Antibody from rCHO Cells in a Centritech Lab Il Centrifuge System," Biotechnology Progress, 2007, 23(5):1186-1197.
Kim et al., "Improved cosmetic activity by optimizing the Lithospermum erythrorhizon extraction process," Cytotechnology, Jan. 2015, 67:51-65.
Kim et al., "Limited Use of Centritech Lab II Centrifuge in Perfusion Culture of rCHO Cells for the Production of Recombinant Antibody," Biotechnology Progress, Jan. 2008, 24(1):166-174.
Kinna et al., "IMAC capture of recombinant protein from unclarified mammalian cell feed streams," Biotechnology and Bioengineering, Jan. 2016, 113(1):130-140.
Kitano et al., "Production of human monoclonal antibodies by heterohybridomas," Applied Microbiology and Biotechnology, Jul. 1986, 24(4):282-286.
Klutz et al., "Continuous viral inactivation at low pH value in antibody manufacturing," Chemical Engineering and Processing: Process Intensification, Apr. 2015, 102:88-101.
Klutz et al., "Developing the biofacility of the future based on continuous processing and single-use technology," Journal of Biotechnology, Nov. 2015, 213:120-130.
Klutz et al., "Narrow residence time distribution in tubular reactor concept for Reynolds No. range of 10-100," Chemical Engineering Research and Design, Mar. 2015, 95:22-33.
Kohara et al., "Enhanced Settling of Mammalian Cells in Tanks with Inclined Plates/ Simulation by Fluid Mechanical Model and Experiment," Journal of Chemical Engineering of Japan, Jun. 1995, 28(6):703-707.

(56) References Cited

OTHER PUBLICATIONS

Kostova et al., "Preparative 42, 43, Chromatographic Separation Of Amino Acid 46-49 Racemic Mixturesl. Adsorption Isotherms," Separation And Purification Technology, 54(3):340-348.
Krober et al., "Continuous purification of influenza virus using simulated moving bed chromatography," Journal of Chromatography A, Sep. 2013, 1307:99-110.
Kula et al., "Protein Purification, Aqueous Liquid Extraction," Encyclopedia of Bioprocess Technology: Fermentation, Biocatalysis, and Bioseparation, Oct. 2002, 29 pages.
Kumar et al., "Type-specific separation of animal cells in aqueous two-phase systems using antibody conjugates with temperature-sensitive polymers," Biotechnology and Bioengineering, Oct. 2001, 75(5):570-580.
Kurnik et al., "Buffer exchange using size exclusion chromatography, countercurrent dialysis, and tangential flow filtration: Models, development, and industrial application," Biotechnology and Bioengineering, Jan. 1995, 45 (2):149-157.
Kyung et al., "High density culture of mammalian cells with dynamic perfusion based on on-line oxygen uptake rate measurements," Cytotechnology, Jan. 1994, 14(3):183-190.
Laird, "Continuous processes in small-scale manufacture," Organic Process Research & Development, 2007, 11 (6):927.
Lawton et al., "Continuous Crystallization of Pharmaceuticals Using a Continuous Oscillatory Baffled Crystallizer," Organic Process Research Development, Oct. 2009, 13(6): 1357-1363.
Lay et al., "Continuous Radial Flow Chromatography of Proteins," Food and Bioproducts Processing, Mar. 2006, 84 (1):78-83.
Li et al., "Design of a UV-C irradiation process for the inactivation of viruses in protein solutions," Biologicals, Jun. 2005, 33(2):101-110.
Li et al., "Multistage Continuous Mixed-Suspension, Mixed-Product Removal (MSMPR) Crystallization with Solids Recycle," Organic Process Research & Development, Dec 2015, 20(2):510-516.
Lin et al., "Evaluation and characterization of axial distribution in expanded bed. I. Bead size, bead density and local bed voidage," Journal of Chromatography A, Aug. 2013, 1304:78-84.
Liu et al., "Recovery and Purification Process Development for Monoclonal Antibody Production," MAbs, Sep. 2010, 5:480-499.
Lorenz et al., "The effect of low intensity ultraviolet-C light on monoclonal antibodies," Biotechnology Progress, Apr. 2009, 25(2):476-482.
Office Action in Canadian Appln. No. 2,965,478, mailed on Sep. 21, 2021, 4 pages.
Office Action in Canadian Appln. No. 3,034,092, mailed on Aug. 16, 2023, 4 pages.
Office Action in Canadian Appln. No. 3, 110,666, mailed on Nov. 7, 2023, 4 pages.
Office Action in Canadian Appln. No. 3092675, mailed on Oct. 22, 2024, 5 pages.
Office Action in Chinese Appln. No. 201480025731.X, mailed on Aug. 3, 2020, 28 pages.
Office Action in Chinese Appln. No. 201480025731.X, mailed on Dec. 4, 2019, 24 pages.
Office Action in Chinese Appln. No. 201480025731.X, mailed on Jun. 5, 2018, 24 pages.
Office Action in Chinese Appln. No. 201480062402.2, mailed on Apr. 23, 2018, 21 pages (with English translation).
Office Action in Chinese Appln. No. 201480062402.2, mailed on Aug. 14, 2020, 17 pages (with English translation).
Office Action in Chinese Appln. No. 201480062402.2, mailed on Aug. 25, 2020, 14 pages (with English translation).
Office Action in Chinese Appln. No. 201480062402.2, mailed on Dec. 21, 2020, 10 pages (with English translation).
Office Action in Chinese Appln. No. 201480062402.2, mailed on Feb. 28, 2017, 19 pages (with English translation).
Office Action in Chinese Appln. No. 201480062402.2, mailed on Nov. 6, 2017, 20 pages (with English translation).
Office Action in Chinese Appln. No. 201580012458.1, mailed on Jan. 14, 2019, 15 pages.
Office Action in Chinese Appln. No. 201580012458.1, mailed on Jun. 26, 2019, 12 pages.
Office Action in Chinese Appln. No. 201580012458.1, mailed on Mar. 2, 2022, 16 pages (with English translation).
Office Action in Chinese Appln. No. 201580012458.1, mailed on Nov. 22, 2019, 14 pages.
Office Action in Chinese Appln. No. 201580012461.3, mailed on May 19, 2017, 26 pages.
Office Action in Chinese Appln. No. 201580070285.9, mailed on Feb. 3, 2019, 22 pages.
Office Action in Chinese Appln. No. 201580070285.9, mailed on Jan. 8, 2021, 7 pages.
Office Action in Chinese Appln. No. 201580070285.9, mailed on May 27, 2020, 9 pages.
Office Action in Chinese Appln. No. 201780063527.0, mailed on Feb. 4, 2023, 12 pages (with English translation).
Office Action in Chinese Appln. No. 201780063527.0, mailed on Jul. 5, 2022, 19 pages (with English translation).
Office Action in Chinese Appln. No. 201810068063.9, mailed on Nov. 1, 2019, 4 pages.
Office Action in Chinese Appln. No. 201980028453.6, mailed on Jun. 12, 2024, 23 pages (with English translation).
Office Action in Chinese Appln. No. 201980028453.6, mailed on Jun. 24, 2023, 34 pages (with English translation).
Office Action in Chinese Appln. No. 201980028453.6, mailed on Nov. 29, 2023, 31 pages (with English translation).
Office Action in Chinese Appln. No. 201980055754.8, mailed on Aug. 3, 2022, 25 pages (with English translation).
Office Action in Chinese Appln. No. 201980055754.8, mailed on Mar. 10, 2022, 32 pages (with English translation).
Office Action in Chinese Appln. No. 202080036857.2, mailed on Feb. 29, 2024, 28 pages (with English translation).
Office Action in Chinese Appln. No. 202080036857.2, mailed on May 20, 2024, 5 pages.
Office Action in Chinese Appln. No. 202080036857.2, mailed on Sep. 12, 2023, 30 pages (with English translation).
Office Action in Chinese Appln. No. 202110234907.4, mailed on Jun. 24, 2023, 9 pages (with English translation).
Office Action in Chinese Appln. No. 202110310605.0, mailed on Jun. 16, 2023, 12 pages (with English translation).
Office Action in Chinese Appln. No. 202110310605.0, mailed on Nov. 7, 2023, 9 pages (with English translation).
Office Action in Eurasian Appln. No. 201690602, mailed on Dec. 7, 2017, 6 pages (with English translation).
Office Action in Eurasian Appln. No. 201690602, mailed on Jun. 20, 2018, 12 pages (with English translation).
Office Action in Eurasian Appln. No. 201892084, mailed on Jan. 16, 2020, 9 pages (with English translation).
Office Action in European AppIn No. 19715277.0, mailed on Jul. 5, 2022, 8 pages.
Office Action in European AppIn No. 19715277.0, mailed on Jun. 21, 2024, 10 pages.
Office Action in European AppIn No. 19715277.0, mailed on Oct. 20, 2020, 4 pages.
Office Action in European Appln. No. 14714835.7, mailed on Nov. 29, 2021, 6 pages.
Office Action in European Appln. No. 15702074.4, mailed on Jan. 24, 2023, 4 pages.
Office Action in European Appln. No. 15702074.4, mailed on Oct. 5, 2021, 6 pages.
Office Action in European Appln. No. 19762543.7, mailed on Jan. 2, 2024, 5 pages.
Office Action in European Appln. No. 19762543.7, mailed on Oct. 31, 2024, 5 pages.
Office Action in Indian Appln. No. 201637009009, mailed on Jul. 2, 2021, 8 pages.
Office Action in Indian Appln. No. 201637024705, mailed on Mar. 25, 2019, 8 pages.
Office Action in Indian Appln. No. 201637025585, mailed on Mar. 6, 2020, 11 pages.

(56) References Cited

OTHER PUBLICATIONS

Office Action in Indian Appln. No. 201637024705, mailed on Aug. 26, 2020, 5 pages.
Office Action in Indian Appln. No. 201737017730, mailed on Dec. 30, 2020, 9 pages.
Office Action in Indian Appln. No. 201917009564, mailed on Jan. 4, 2021, 9 pages.
Office Action in Indian Appln. No. 202037042608, mailed on Aug. 11, 2022, 8 pages.
Office Action in Indian Appln. No. 202137013657, mailed on Aug. 4, 2022, 7 pages.
Office Action in Indian Appln. No. 2978/KOLNP/2015, mailed on Jun. 7, 2019, 12 pages.
Office Action in Indian Appln. No. 2978/KOLNP/2015, mailed on Nov. 6, 2020, 8 pages.
Office Action in Indonesian Appln. No. P00202007144, mailed on Nov. 2, 2023, 5 pages (with English translation).
Office Action in Indonesian Appln. No. P00202102143, mailed on Feb. 20, 2023, 3 pages.
Office Action in Indonesian Appln. No. P00202102143, mailed on Oct. 12, 2022, 7 pages (with English translation).
Office Action in Israel Appln. No. 251819, mailed on May 23, 2019, 9 pages.
Office Action in Israeli Appln. No. 240792, mailed on Jul. 17, 2017, 3 pages.
Office Action in Israeli Appln. No. 240792, mailed on Jul. 31, 2018, 7 pages.
Office Action in Israeli Appln. No. 240792, mailed on Jun. 23, 2019, 8 pages.
Office Action in Israeli Appln. No. 244552, mailed on Dec. 29, 2019, 76 pages (with English translation).
Office Action in Israeli Appln. No. 244552, mailed on Sep. 17, 2018, 6 pages (with English translation).
Office Action in Israeli Appln. No. 246774, mailed on Jun. 12, 2019, 8 pages.
Office Action in Israeli Appln. No. 246774, mailed on Oct. 22, 2019, 11 pages.
Office Action in Israeli Appln. No. 264828, mailed on Feb. 9, 2020, 4 pages (with English translation).
Office Action in Israeli Appln. No. 264828, mailed on Oct. 17, 2023, 4 pages (with English translation).
Office Action in Israeli Appln. No. 274646, mailed on Apr. 8, 2021, 8 pages.
Office Action in Israeli Appln. No. 275181, mailed on Nov. 4, 2020, 126 pages.
Office Action in Israeli Appln. No. 281077, mailed on Feb. 2, 2026, 6 pages.
Office Action in Israeli Appln. No. 281077, mailed on Jan. 29, 2025, 9 pages (English summary).
Office Action in Japanese Appln. No. 2015-561502, mailed on Apr. 3, 2018, 6 pages.
Office Action in Japanese Appln. No. 2015-561502, mailed on Feb. 26, 2019, 6 pages.
Office Action in Japanese Appln. No. 2016-542875, mailed on Dec. 17, 2019, 4 pages (with English translation).
Office Action in Japanese Appln. No. 2016-542875, mailed on Feb. 24, 2021, 7 pages (with English translation).
Office Action in Japanese Appln. No. 2016-542875, mailed on Jul. 10, 2018, 18 pages (with English translation).
Office Action in Japanese Appln. No. 2016-542875, mailed on May 14, 2019, 9 pages (with English translation).
Office Action in Japanese Appln. No. 2016-546935, mailed on Jun. 12, 2019, 3 pages.
Office Action in Japanese Appln. No. 2016-546935, mailed on Oct. 16, 2018, 5 pages.
Office Action in Japanese Appln. No. 2016-546971, mailed on Aug. 6, 2019, 5 pages.
Office Action in Japanese Appln. No. 2016-546971, mailed on Dec. 4, 2018, 16 pages.
Office Action in Japanese Appln. No. 2017-522117, mailed on Jul. 23, 2019, 7 pages.
Office Action in Japanese Appln. No. 2019-131561, mailed on Apr. 6, 2021, 2 pages.
Office Action in Japanese Appln. No. 2019-131561, mailed on Aug. 25, 2020, 9 pages.
Office Action in Japanese Appln. No. 2019-192394, mailed on Apr. 6, 2021, 10 pages.
Office Action in Japanese Appln. No. 2019-192394, mailed on Dec. 8, 2020, 9 pages.
Office Action in Japanese Appln. No. 2019-192394, mailed on Jul. 12, 2022, 10 pages (with English translation).
U.S. Appl. No. 61/420,066, Ransohoff.
U.S. Appl. No. 61/775,060, Konstantinov et al.
U.S. Appl. No. 61/856,390, Konstantinov et al.
U.S. Appl. No. 61/878,502, Zhou et al.
U.S. Appl. No. 61/928,906, Godawat et al.
U.S. Appl. No. 61/928,929, Godawat et al.
U.S. Appl. No. 62/001,498, Godawat et al.
"Cross Flow Filtration Method Handbook," dated Jan. 1, 2014, retrieved from the Internet: URL: https://www.gelifesciences.com/gehcls_images/GELS/Related%20Content/Flles/1392028292867/litdoc29085076_20140313045908.pdf [retrieved on Jun. 26, 2015].
Acharya, "Mannitol Salt Agar (MSA): Composition, uses and colony characteristics," Microbe Online, Aug. 2013, 7 pages.
Acikara, "lon-Exchange Chromatography and its Applications," col. Chromatography, Chapter 2, Apr. 10, 2013, pp. 31-58.
Acmerevival.com [online], "Watson-Marlow 620UN / 620U, 620SN / 620S pumps," Jul. 5, 2024, retrieved on Aug. 23, 2024, retrieved from URL <https://acmerevival.com/wp-content/uploads/2021/07/Watson-Marlow-620U-User-Manual. pdf>, 100 pages.
Acrivos et al., "Enhanced sedimentation in settling tanks with inclined walls," Journal of Fluid Mechanics, 1979, 92 (3):435-457.
Al-Rubeai, "Antibody expression and Production," Cell Engineering, May 2011, pp. 34-39.
Anderson, "Practical use of continuous processing in developing and development scaling up laboratory processes," Org. Proc. Res. Dev., 2001, 5(6):613-621.
Aniceto et al., "Simulated Moving Bed Strategies and Designs: From Established Systems to the Latest Developments," Separation & Purification Reviews, 2015, 44(1):41-73.
Anspach et al., "Expanded-bed chromatography in primary protein purification," Journal of Chromatography A, Dec 1999, 865(1-2): 129-144.
Appeal Decision in Japanese Patent Application No. 2021-10168, dated Nov. 29, 2022, 13 pages (with English translation).
Arunkumar et al., "Investigation of single-pass tangential flow filtration (SPTFF) as an inline concentration step for cell culture harvest," Journal of Membrane Science, Feb. 15, 2017, 524:20-32.
Asakura et al., "Ethanol production by high cell-density culture with periodic reversion of circulating flow in cross-flow filtration," The Society for Bioscience and Bioengineering, 1991, 69(4):225-232 (with English translation).
Aumann et al., "A Continuous Multicolumn Countercurrent Solvent Gradient Purification (MCSGP) Process," Biotechnology and Bioengineering, Dec 2007, 98(5):1043-1055.
Aumann et al., "A semicontinuous 3-col. countercurrent solvent gradient purification (MCSGP) process," Biotechnology and Bioengineering, Feb. 2008, 99(3):728-733.
Avgerinos et al., "Spin Filter Perfusion System for High Density Cell Culture: Production of Recombinant Urinary Type Plasminogen Activator in CHO Cells," Nature Biotechnology, Jan. 1990, 8(1):54-58.
Azevedo et al., "Chromatography-free recovery of biopharmaceuticals through aqueous two-phase processing," Trends in Biotechnology, Apr. 2009, 27(4):240-247.
Azevedo et al., "Partitioning of human antibodies in polyethylene glycol-sodium citrate aqueous two-phase systems," Separation and Purification Technology, Feb. 2009, 65(1):14-21.
Bae et al., "Evaluation of Viral Inactivation Efficacy of a Continuous Flow Ultraviolet-C Reactor (UVivatec)," Korean Journal of Microbiology and Biotechnology, Dec 2009, 37(4):377-382.

(56) References Cited

OTHER PUBLICATIONS

Ballew et al., "The ABCs Of Filtration and Bioprocessing For The Third Millennium," SpectrumLabs.com, 2002, 163 pages.
Balmert et al., "Perfusion circuit concepts for hollow-fiber bioreactors used as in vitro cell production systems or ex vivo bioartificial organs," The International Journal of Artificial Organs, May 2011, 34(5):1-13.
Basu et al., "Protein crystals for the delivery of biopharmaceuticals," Expert Opinion on Biological Therapy, 2004, 4 (3):301-317.
Belfort et al., "The behavior of suspensions and macromolecular solutions in crossflow microfiltration," Journal of Membrane Science, 1994, 96:1-58.
Bell et al., "The Formation of Protein Precipitates and Their Centrifugal Recovery," Downstream Processing, 1983, pp. 1-72.
Berger et al., "Minimizing UV noise in supercritical fluid chromatography. I. Improving back pressure regulator pressure noise," Journal of Chromatography A, Apr. 22, 2011, 1218(16):2320-2326.
Berthod et al., "Analytical Separation Science," First Edition, Wiley-VCH Verlag GmbH & Co., 2015, pp. 1177-1260.
Besselink et al., "Are axial and radial flow chromatography different?," Journal of Chromatography A, Jan. 2013, 1271(1): 105-114.
Bierau et al., "A comparison of intensive cell culture bioreactors operating with Hybridomas modified for inhibited apoptotic response," Journal of Biotechnology, Jul. 1998, 62(3):195-207.
Bisschops et al., "Single-Use, Continuous-Countercurrent, Multicolumn Chromatography," BioProcess International, Supplement, Jun. 1, 2009, pp. 18-23.
Blank et al., "Self-Immobilizing Recombinant antibody Fragments for Immunoaffinity Chromatography: Generic, Parallel, and Scalable Protein Purification," Protein Expression and Purification, Mar. 1, 2002, 24:313-322.
Blaschczok et al., "Investigations on Mechanical Stress Caused to CHO Suspension Cells by Standard and Single-Use Pumps," Chemie Ingenieur Technik, Nov. 2012, 85(1-2):144-152.
Bloomingburg et al., "Separation of protein mixtures by continuous annular chromatography with step elution," The Chemical Engineering Journal and the Biochemical Engineering Journal, Aug. 1994, 55(1-2):B19-B274.
Boegger Industech Limited, "Packed tower- working principle and advantages in industrial filtering," Nov. 2017, retrieved on Sep. 22, 2022, retrieved from URL <https://www.demisterpads.com/demister-pad/packed-tower. html>, 4 pages.
Boycott et al., "Sedimentation of Blood Corpuscles," Nature, Jan. 1920, 104:532.
Brennan et al., "A perfusion system for antibody production by shear-sensitive hybridoma cells in a stirred reactor," Biotechnology Techniques, Sep. 1987, 1(3):169-174.
Bridges et al., "Continuous Cross-Current Chromatographic Refiners," Preparative and Production Scale Chromatography, 1992, 61:113-126.
Brief Communication in Opposition against European Appln. No. 14780959.4, dated Aug. 21, 2023, 12 pages.
Brief Communication in Opposition against European Appln. No. 14780959.4, dated Aug. 24, 2023, 8 pages.
Brief Communication in Opposition against European Appln. No. 14780959.4, dated Jun. 30, 2022, 5 pages.
Brief Communication in Opposition against European Appln. No. 14780959.4, dated Oct. 18, 2022, 27 pages.
Bro et al., "Principal component analysis," Analytical Methods, 2014, 6:2812-2831.
Brodsky et al., "Caprylic acid precipitation method for impurity reduction: An alternative to conventional chromatography for monoclonal antibody purification," Biotechnology and Bioengineering, Apr. 2012, 109 (10):2589-2598.
Brower et al., "What Can Continuous Processing Do For You?," Biopharmaceutical Development & Production Week Conference, Huntington Beach, CA, Feb. 28, 2013, 27 pages.
Buchacher et al., "Purification of intravenous immunoglobulin G from human plasma—aspects of yield and virus safety," Biotechnology Journal, Feb. 2006, 1(2):148-163.
Cabanne et al., "Evaluation of radial chromatography versus axial chromatography, practical approach," Journal of Chromatography B, Jan. 2007, 845(2):191-199.
Caillet-Fauquet et al., "Continuous-flow UVC irradiation: a new, effective, protein activity-preserving system for inactivating bacteria and viruses, including erythrovirus B19," Journal of Virological Methods, Jun. 2004, 118 (2):131-139.
Casey et al., "Protein concentration with single-pass tangential flow filtration (SPTFF)," Journal of Membrane Science, Nov. 15, 2011, 384(2):82-88.
Castilho et al., "An integrated process for mammalian cell perfusion cultivation and product purification using a dynamic filter," Biotechnol. Prog., Jul. 2002, 18(4):776-781.
Castilho et al., "Animal cell separation," Animal Cell Technology: From Biopharmaceuticals to Gene Therapy, 2008, pp. 273-294.
Castilho et al., "Cell Retention Devices for Suspended-Cell Perfusion Cultures," Advances in Biochemical Engineering and Biotechnology, 2002, 74:129-169.
Cell Culture Technology For Pharmaceutical and Cell-Based Therapies, Ozturk and Hu (ed)., 2006, Chapter 6 and 11, 103 pages.
Office Action in U.S. Appl. No. 14/195,481, mailed on Apr. 29, 2016, 50 pages.
Office Action in U.S. Appl. No. 14/195,481, mailed on Sep. 22, 2015, 25 pages.
Office Action in U.S. Appl. No. 14/598,401, mailed on Apr. 19, 2016, 7 pages.
Office Action in U.S. Appl. No. 14/598,401, mailed on Jun. 2, 2017, 8 pages.
Office Action in U.S. Appl. No. 14/598,401, mailed on Oct. 18, 2016, 4 pages.
Office Action in U.S. Appl. No. 14/598,450, mailed on Aug. 3, 2017, 23 pages.
Office Action in U.S. Appl. No. 14/598,450, mailed on Feb. 21, 2018, 30 pages.
Office Action in U.S. Appl. No. 14/627,559, mailed on Oct. 1, 2015, 17 pages.
Office Action in U.S. Appl. No. 14/627,674, mailed on Apr. 21, 2015, 9 pages.
Office Action in U.S. Appl. No. 14/627,674, mailed on Aug. 4, 2015, 10 pages.
Office Action in U.S. Appl. No. 14/627,674, mailed on Feb. 1, 2018, 12 pages.
Office Action in U.S. Appl. No. 14/627,674, mailed on Feb. 11, 2019, 8 pages.
Office Action in U.S. Appl. No. 14/627,674, mailed on Jun. 19, 2017, 10 pages.
Office Action in U.S. Appl. No. 14/627,674, mailed on May 18, 2016, 12 pages.
Office Action in U.S. Appl. No. 14/627,674, mailed on Nov. 29, 2016, 13 pages.
Office Action in U.S. Appl. No. 14/627,674, mailed on Oct. 30, 2018, 11 pages.
Office Action in U.S. Appl. No. 14/629,315, mailed on Mar. 8, 2016, 5 pages.
Office Action in U.S. Appl. No. 14/629,315, mailed on May 19, 2015, 5 pages.
Office Action in U.S. Appl. No. 14/629,315, mailed on Oct. 20, 2015, 8 pages.
Office Action in U.S. Appl. No. 14/629,356, mailed on Aug. 29, 2016, 15 pages.
Office Action in U.S. Appl. No. 14/629,356, mailed on Feb. 10, 2016, 13 pages.
Office Action in U.S. Appl. No. 14/629,356, mailed on Feb. 22, 2017, 14 pages.
Office Action in U.S. Appl. No. 14/629,356, mailed on Jan. 4, 2018, 15 pages.
Office Action in U.S. Appl. No. 14/629,356, mailed on Jul. 7, 2015, 16 pages.
Office Action in U.S. Appl. No. 14/645,138, mailed on Feb. 18, 2016, 17 pages.
Office Action in U.S. Appl. No. 14/645,138, mailed on Sep. 22, 2015, 14 pages.

(56) References Cited

OTHER PUBLICATIONS

Office Action in U.S. Appl. No. 14/918,107, mailed on Dec. 19, 2017, 9 pages.
Office Action in U.S. Appl. No. 14/918,107, mailed on Jul. 27, 2018, 10 pages.
Office Action in U.S. Appl. No. 14/918,107, mailed on Mar. 26, 2019, 10 pages.
Office Action in U.S. Appl. No. 14/918,107, mailed on May 21, 2020, 17 pages.
Office Action in U.S. Appl. No. 14/918,107, mailed on Nov. 1, 2019, 11 pages.
Office Action in U.S. Appl. No. 15/493,523, mailed on Mar. 13, 2019, 7 pages.
Office Action in U.S. Appl. No. 15/493,523, mailed on Oct. 17, 2019, 15 pages.
Office Action in U.S. Appl. No. 15/677,888, mailed on Aug. 12, 2020, 11 pages.
Office Action in U.S. Appl. No. 15/677,888, mailed on Feb. 28, 2020, 11 pages.
Office Action in U.S. Appl. No. 15/677,888, mailed on Nov. 14, 2019, 16 pages.
Office Action in U.S. Appl. No. 16/107,110, mailed on May 14, 2020, 4 pages.
Office Action in U.S. Appl. No. 16/107,110, mailed on Oct. 4, 2019, 17 pages.
Office Action in U.S. Appl. No. 16/107,203, mailed on Apr. 16, 2020, 37 pages.
Office Action in U.S. Appl. No. 16/107,203, mailed on Apr. 26, 2019, 12 pages.
Office Action in U.S. Appl. No. 16/107,203, mailed on Jan. 9, 2020, 32 pages.
Office Action in U.S. Appl. No. 16/107,203, mailed on Sep. 13, 2018, 8 pages.
Office Action in U.S. Appl. No. 16/107,203, mailed on Sep. 6, 2019, 18 pages.
Office Action in U.S. Appl. No. 16/290,713, mailed on Feb. 15, 2024, 10 pages.
Office Action in U.S. Appl. No. 16/543,247, mailed on Aug. 19, 2021, 5 pages.
Office Action in U.S. Appl. No. 16/543,247, mailed on Feb. 19, 2021, 5 pages.
Office Action in U.S. Appl. No. 16/837,126, mailed on Feb. 3, 2023, 23 pages.
Office Action in U.S. Appl. No. 16/837,126, mailed on May 25, 2023, 24 pages.
Office Action in U.S. Appl. No. 16/837,126, mailed on Oct. 21, 2022, 22 pages.
Office Action in U.S. Appl. No. 16/908,401, mailed on Aug. 18, 2022, 17 pages.
Office Action in U.S. Appl. No. 16/908,401, mailed on Feb. 28, 2022, 17 pages.
Office Action in U.S. Appl. No. 16/908,401, mailed on Feb. 28, 2024, 9 pages.
Office Action in U.S. Appl. No. 16/908,401, mailed on Jan. 11, 2023, 17 pages.
Office Action in U.S. Appl. No. 16/908,401, mailed on Jul. 6, 2023, 16 pages.
Office Action in U.S. Appl. No. 16/908,401, mailed on Nov. 6, 2023, 20 pages.
Office Action in U.S. Appl. No. 16/908,401, mailed on Oct. 26, 2021, 15 pages.
Office Action in U.S. Appl. No. 16/993,654, mailed on Jun. 28, 2023, 16 pages.
Office Action in U.S. Appl. No. 17/027,017, mailed on Aug. 29, 2024, 12 pages.
Office Action in U.S. Appl. No. 17/027,017, mailed on Dec. 9, 2024, 12 pages.
Office Action in U.S. Appl. No. 17/027,017, mailed on Jan. 23, 2024, 11 pages.
Office Action in U.S. Appl. No. 17/027,017, mailed on Oct. 27, 2023, 11 pages.
Office Action in U.S. Appl. No. 17/149,613, mailed on Apr. 24, 2023, 5 pages.
Office Action in U.S. Appl. No. 17/149,613, mailed on Oct. 5, 2022, 7 pages.
Office Action in U.S. Appln. No. 17/321, 128, mailed on Feb. 6, 2023, 9 pages.
Office Action in U.S. Appl. No. 17/321,128, mailed on Jun. 26, 2023, 9 pages.
Office Action in U.S. Appl. No. 17/321,128, mailed on Oct. 17, 2022, 8 pages.
Office Action in U.S. Appl. No. 17/456,504, mailed on Jan. 9, 2023, 12 pages.
Office Action in U.S. Appl. No. 17/456,504, mailed on Mar. 21, 2022, 11 pages.
Office Action in U.S. Appl. No. 17/456,504, mailed on Sep. 21, 2023, 5 pages.
Office Action in U.S. Appl. No. 17/456,504, mailed on Sep. 8, 2022, 10 pages.
Office Action in U.S. Appln. No. 17/643, 128, mailed on Dec. 19, 2022, 14 pages.
Office Action in U.S. Appl. No. 17/643,128, mailed on Feb. 11, 2022, 16 pages.
Office Action in U.S. Appl. No. 17/643,128, mailed on May 18, 2022, 15 pages.
Office Action in U.S. Appl. No. 17/643,128, mailed on May 26, 2023, 15 pages.
Office Action in U.S. Appl. No. 17/643,128, mailed on Oct. 6, 2023, 15 pages.
Office Action in U.S. Appl. No. 18/174,575, mailed on Sep. 5, 2025, 17 pages.
Shintani et al., "Comparison of culture methods for human-human hybridomas secreting anti-HBsAg human monoclonal antibodies," Cytotechnology, Jul. 1991, 6(3):197-208.
Shirgaonkar et al., "Acoustic cell filter: a proven cell retention technology for perfusion of animal cell cultures," Biotechnology Advances, Jul. 2004, 22(6):433-444.
Singh et al., "Clarification technologies for monoclonal antibody manufacturing processes: Current state and future perspectives," Biotechnology and Bioengineering, Aug. 2015, 113(4):698-716.
Smith et al., "Experience in scale-up of homogeneous perfusion culture for hybridomas," Bioprocess Engineering, 1991, 6:213-219.
Smith et al., "Hydrophobic interaction ligand selection and scale-up of an expanded bed separation of an intracellular enzyme from Saccharomyces cerevisiae," Journal of Chromatography A, Aug. 2002, 968 (1):121-128.
Sommer et al., "Combined polyethylene glycol and CaCI2 precipitation for the capture and purification of recombinant antibodies," Process Biochemistry, Nov. 2014, 49(11):2001-2009.
Spectrum Laboratories, Inc, "Conversion of Bioreactors to Continuous Perfusion Using Hollow Fiber Cell Separators," 1989, 30 pages.
Styskin et al., "Gas Chromatography of 42,45,51 Phenolic Antioxidants," Journal of Chromatography, 1973, 77 (1):11-19.
Su et al., "Pharmaceutical crystallisation processes from batch to continuous operation using MSMPR stages: Modelling, design, and control," Chemical Engineering Processing: Process Intensification, Mar. 2015, 89:41-53.
Subramanian G. (Ed.), Continuous Processing in Pharmaceutical Manufacturing, Wiley-VCH, Weinheim, Germany, 2014.
Sun et al., "Chromatography of human prothrombin from Nitschmann fraction III on DEAE Sepharose Fast Flow using axial and radial flow column," Biomedical Chromatography, Nov. 2000, 14(7):478-482.
Supplemental Information from Mueller-Spath et al., "Two Step Capture and Purification Purification of IgG2 Using Multicolumn Countercurrent Solvent Gradient Purification (MCSGP)," Biotechnol. Bioeng., Jul. 30, 2010, 107 (6):974-984.
Svensson et al., "Thermally controlled microfluidic back pressure regulator," Scientific Reports, 2022, 12:569.

(56) References Cited

OTHER PUBLICATIONS

Takahashi et al., "Continuous Separations of Amino Acids by Using an Annular Chromatograph with Rotating Inlet and Outlet," Separation Science and Technology, 1991, 26(1):1-13.
Takamatsu et al., "Large-scale perfusion culture process for suspended mammalian cells that uses a centrifuge with multiple settling zones," Applied Microbiology and Biotechnology, May 1996, 45(4):454-457.
Takazawa et al., "High cell density perfusion culture of mouse-human hybridomas," Applied Microbiology and Biotechnology, Dec 1989, 32(3):280-284.
Tao et al., "Development and implementation of a perfusion-based high cell density cell banking process," Biotechnology Progress, Mar. 2011, 27(3):824-829.
Tharakan et al., "Ligand efficiency in axial and radial flow immunoaffinity chromatography of factor IX," Journal of Chromatography A, May 1995, 702(1):191-196.
Thommes, "Fluidized Bed Absorption as a Primary Recovery Step in Protein Purification," New Enzymes for Organic Synthesis, 1997, pp. 185-230.
Tokashiki et al., "High density culture of hybridoma cells using a perfusion culture vessel with an external centrifuge," Cytotechnology, May 1990, 3(3):239-244.
Tolbert et al., "Large-scale rotating filter perfusion system for high-density growth of mammalian suspension cultures," In Vitro, Oct. 1981, 17(10):885-890.
Tricorn 5/20 column, GE Healthcare Life Sciences, Retrieved on Sep. 17, 2015, 1 page.
Tscheliessnig et al., "Ethanol precipitation for purification of recombinant antibodies," Journal of Biotechnology, Oct. 2014, 188:17-28.
Tyo et al., "Dense cultures of animal cells at the industrial scale," Enzyme and Microbial Technology, Sep. 1987, 9(9):514-520.
United States Environment Protection Agency, "Wastewater Technology Fact Sheet Ozone Disinfection," EPA, Sep. 1999, retrieved from URL <www3.epa.gov/npdes/pubs/ozon.pdf>, 7 pages.
Vallez-Chetreaunu et al., "An on-line method for the reduction of fouling of spin-filters for animal cell perfusion cultures," Journal of Biotechnology, Jun. 2007, 130(3):265-273.
Van Reis et al., "Industrial scale harvest of proteins from mammalian cell culture by tangential flow filtration," Biotechnology and Bioengineering, Aug. 5, 1991, 38(4):413-422.
Van Walsem et al., "Simulated moving bed in the production of lysine," Journal of Biotechnology, Dec 1997, 59:127-132.
Vazquez-Villegas et al., "Continuous enzyme aqueous two-phase extraction using a novel tubular mixer-settler in multi-step countercurrent arrangement," Separation and Purification Technology, Feb. 2015, 141:263-268.
Velez et al., "Use of Tangential Flow Filtration in Perfusion Propagation of Hybridoma Cells for Production of Monoclonal Antibodies," Biotechnology and Bioengineering, 1989, 33(7):938-940.
Vogel et al., "Continuous annular chromatography: General characterization and application for the isolation of recombinant protein drugs," Biotechnology and Bioengineering, Sep. 2002, 80(5):559-568.
Vogel et al., "A new large-scale manufacturing platform for complex biopharmaceuticals," Biotechnology and Bioengineering, Jun. 2012, 109(12):3049-3058.
Wang et al., "A simple apparatus for measuring cell settling velocity," Biotechnology Progress, Mar. 2010, 26 (5):1361-1366.
Wang et al., "Virus inactivation and protein recovery in a novel ultraviolet-C reactor," Vox Sanguinis, 2004, 86 (4):230-238.
Warikoo et al., "A new use for existing technology—continuous precipitation for purification of recombination proteins," Biotechnology Journal, Mar. 2015, 10(8):1101-1102.
Warikoo et al., "Integrated continuous production of recombinant therapeutic proteins," Biotechnology and Bioengineering, Jun. 2012, 109(12):3018-3029.
Watercareproducts.com.sg [online], "Pressure Regulator vs. Backpressure Regulator," Jan. 19, 2016, retrieved on Sep. 3, 2025, retrieved from URL <https://www.watercareproducts.com.sg/filestore/full/118catalogdownload. pdf>, 4 pages.
Low et al., "Future of antibody purification," Journal of Chromatography B, Mar. 2007, 848(1):48-63.
Lydersen et al., "Acid precipitation of mammalian cell fermentation broth," Annals of the New York Academy of Sciences, Nov. 1994, 745(1):222-231.
Mahajan et al., "Improving affinity chromatography resin efficiency using semi-continuous chromatography," Journal of Chromatography A, Mar. 2012, 1227:154-162.
Martin et al., "Novel small scale TFF cell retention device for perfusion cell culture systems," BMC Proceedings, 2015, 9(Suppl 9): P25, 2 pages.
Martin, "Summarizing Paper," Discussions of the Faraday Society, Oct. 1949, 7:332-336.
Mascia et al., "End-to-End Continuous Manufacturing of Pharmaceuticals: Integrated Synthesis, Purification, and Final Dosage Formation," Angewandte Chemie International Edition, Oct. 2013, 52(47): 12359-12363.
Mashayekhi et al., "Concentration of mammalian genomic DNA using two-phase aqueous micellar systems," Biotechnology and Bioengineering, Apr. 2009, 102(6):1613-1623.
McNerney et al., "PDADMAC Flocculation of Chinese Hamster Ovary Cells: Enabling a Centrifuge-Less Harvest Process for Monoclonal Antibodies," MAbs, Mar. 2015, 2:413-427.
Medi et al., "Optimal performance of single-col. chromatography and simulated moving bed processes for the separation of optical isomers," IOP Conference Series: Materials Science and Engineering 24, 2013, 10 pages.
Mercille et al., "Filtration-based perfusion of hybridoma cultures in protein-free medium: Reduction of membrane fouling by medium supplementation with DNase I," Biotechnology and Bioengineering, Apr. 1994, 43(9):833-846.
Mercille et al., "Understanding factors that limit the productivity of suspension-based perfusion cultures operated at high medium renewal rates," Biotechnology and Bioengineering, Mar. 2000, 67(4):435-450.
Meuwly et al., "Packed-bed bioreactors for mammalian cell culture: Bioprocess and biomedical applications," Biotechnology Advances, Jan. 2007, 25(1):45-56.
Moore et al., "Protection of Protein A-Sepharose cols. Irradiated to Sterilization Doses," Radiation Physics and Chemistry, Jan. 1996, 47(1):161-165.
Muendges et al., "Multistage aqueous two-phase extraction of a monoclonal antibody from cell supernatant," Biotechnology Progress, Apr. 2015, 31(4):925-936.
Muller-Spath et al., "Chromatographic separation of three monoclonal antibody variants using multicolumn countercurrent solvent gradient purification (MCSGP)," Biotechnology and Bioengineering, Feb. 2008, 100 (6):1166-1177.
Muller-Spath et al., "Increasing the Activity of Monoclonal Antibody Therapeutics by Continuous Chromatography (MCSGP)," Biotechnology and Bioengineering, 2010, 107(4):652-662.
Muller-Spath et al., "Two step capture and purification of lgG2 using multicolumn countercurrent solvent gradient purification (MCSGP)," Biotechnol. Bioengineering, Dec. 2010, 107(6):974-984.
Mun et al., "Optimal Design of a Size-Exclusion Tandem Simulated Moving Bed for Insulin Purification," Industrial & Engineering Chemistry Research, Apr. 2003, 42 (9):1977-1993.
Napadensky et al., "Continuous Countercurrent Tangential Chromatography for Monoclonal Antibody Purification," Separation Science and Technology, Feb. 2013, 48(9): 1289-1297.
Neugebauer et al., "Continuous Crystallization of Proteins in a Tubular Plug-Flow Crystallizer," Crystal Growth & Design, Feb. 2015, 15(3): 1089-1095.
Ng et al., "Regeneration Studies of Anion-Exchange Chromatography Resins," Bioprocess International, May 2007, 5 (5):52-56.
Nicholas et al., "Continuous chromatography apparatus: III. Application," Journal of Chromatography A, 1969, 43:61-65.
Notice of Allowance in Korean Appln. No. 10-2021-7009242, mailed on Mar. 20, 2025, 8 pages (with English translation).

(56) References Cited

OTHER PUBLICATIONS

Notice of Allowance in Mexican Appln. No. MX/a/2020/001823, mailed on Nov. 5, 2025, 10 pages (with English translation).
Notice of Allowance in Mexican Appln. No. MX/a/2021/002314, mailed on Sep. 24, 2025, 18 pages (with English translation).
Notice of Allowance in Mexican Appln. No. MX/a/2021/007792, mailed on Jun. 24, 2025, 17 pages (with English translation).
Notice of Allowance in Singapore Appln. No. 10201709131U, mailed on Nov. 20, 2025, 4 pages.
Notice of Opposition by Konig Szynka Tilmann von Renesse Patentanwalte Partnerschaft mbB in European Appln. No. 14780959.4, mailed on May 27, 2022, 54 pages.
Office Action in Argentinian Appln. No. AR 095064, mailed on Dec. 13, 2019, 5 pages.
Office Action in Australian Appln. No. 2014226126, mailed on Feb. 23, 2018, 5 pages.
Office Action in Australian Appln. No. 2014226126, mailed on Jan. 29, 2019, 3 pages.
Office Action in Australian Appln. No. 2014318420, mailed on Jan. 3, 2020, 3 pages.
Office Action in Australian Appln. No. 2014318420, mailed on Jan. 4, 2019, 3 pages.
Office Action in Australian Appln. No. 2014318420, mailed on Oct. 29, 2019, 3 pages.
Office Action in Australian Appln. No. 2015206341, mailed on Aug. 2, 2019, 3 pages.
Office Action in Australian Appln. No. 2015206341, mailed on Nov. 9, 2018, 6 pages.
Office Action in Australian Appln. No. 2015206422, mailed on Aug. 13, 2019, 5 pages.
Office Action in Australian Appln. No. 2015206422, mailed on May 7, 2020, 4 pages.
Office Action in Australian Appln. No. 2015336130, mailed on Nov. 13, 2019, 8 pages.
Office Action in Australian Appln. No. 2017313042, mailed on Oct. 18, 2023, 6 pages.
Office Action in Australian Appln. No. 2019203128, mailed on Mar. 18, 2020, 6 pages.
Office Action in Australian Appln. No. 2019226568, mailed on Oct. 10, 2023, 3 pages.
Office Action in Australian Appln. No. 2019268188, mailed on Feb. 10, 2022, 2 pages.
Office Action in Australian Appln. No. 2019332764, mailed on Jan. 29, 2025, 3 pages.
Office Action in Australian Appln. No. 2019332764, mailed on May 15, 2024, 3 pages.
Office Action in Australian Appln. No. 2020202568, mailed on May 26, 2021, 3 pages.
Office Action in Australian Appln. No. 2020202568, mailed on Oct. 26, 2021, 4 pages.
Office Action in Australian Appln. No. 2020253381, mailed on Mar. 16, 2026, 2 pages.
Office Action in Australian Appln. No. 2020253381, mailed on Mar. 25, 2025, 3 pages.
Office Action in Australian Appln. No. 2021200474, mailed on Jul. 24, 2023, 3 pages.
Office Action in Taiwanese Appln. No. 108121669, mailed on Apr. 23, 2020, 1 page.
Office Action in Taiwanese Appln. No. 108121669, mailed on Aug. 31, 2020, 11 pages.
Office Action in Taiwanese Appln. No. 108130986, mailed on Apr. 9, 2024, 8 pages (with English summary).
Office Action in Taiwanese Appln. No. 108130986, mailed on Dec. 16, 2025, 9 pages (with English summary).
Office Action in Taiwanese Appln. No. 108130986, mailed on Oct. 18, 2023, 26 pages (with English translation).
Office Action in Taiwanese Appln. No. 109107478, mailed on May 5, 2023, 7 pages (with English translation).
Office Action in Taiwanese Appln. No. 109107478, mailed on Oct. 21, 2022, 9 pages (with machine translation).
Office Action in Taiwanese Appln. No. 109108985, mailed on Aug. 27, 2020, 8 pages (with English translation).
Office Action in Taiwanese Appln. No. 109108985, mailed on May 18, 2021, 9 pages (with English translation).
Office Action in Taiwanese Appln. No. 109127478, mailed on Nov. 3, 2021, 4 pages (with English translation).
Office Action in Taiwanese Appln. No. 113126884, mailed on Dec. 16, 2025, 11 pages (with English summary).
Ohashi et al., "Perfusion cell culture in disposable bioreactors," Animal Cell Technology: From Target to Market, 2001, pp. 403-409.
Opposition, "Applicant's submission in the examination proceedings dated Feb. 5, 2018," Exhibit D1 in European Appln. No. 14780959.4, dated Feb. 5, 2018, 4 pages.
Owen et al., "Direct purification of lysozyme using continuous counter-current expanded bed adsorption," Journal of Chromatography A, Jan. 1997, 757 (1):41-49.
Owen et al., "Modeling of the continuous counter-current expanded bed adsorber for the purification of proteins," Chemical Engineering Science, Sep. 1999, 54(17):3765-3781.
Ozyurt et al., "Recovery of antithrombin III from milk by expanded bed chromatography," Journal of Chromatography A, Jan. 2002, 944(1):203-210.
Padawer et al., "Case Study: An accelerated 8-day monoclonal antibody production process based on high seeding densities," Biotechnology Progress, Apr. 2013, 29(3):829-832.
Pattasseril et al., "Downstream Technology Landscape for Large-Scale Therapeutic Cell Processing," BioProcess International, Mar. 2013, 11(3):38-47.
Peters et al., "Implementation of a crystallization step into the purification process of a recombinant protein," Protein Expression and Purification, Jan. 2005, 39(1):43-53.
Pinto et al., "Separation of CHO cells using hydrocyclones," Cytotechnology, Nov. 2007, 56(1):57-67.
Piret et al., "Immobilized mammalian cell cultivation in hollow fiber bioreactors," Biotechnology Advances, 1990, 8 (4):763-784.
Poechlauer et al., "Continuous Processing in the Manufacture of Active Pharmaceutical Ingredients and Finished Dosage Forms: An Industry Perspective," Organic Process Research & Development, Sep. 2012, 16 (10):1586-1590.
Pohlscheidt et al., "Optimizing capacity utilization by large scale 3000 L perfusion in seed train bioreactors," Biotechnology Progress, Jan. 2013, 29(1):222-229.
Power et al., "Design and optimization of a multistage continuous cooling mixed suspension, mixed product removal crystallizer," Chemical Engineering Science, Sep. 2015, 133:125-139.
Process Scale Purification of Antibodies, Gottschalk (ed)., 2009, Chapter 3, pp. 53-78.
Pui et al., "Batch and Semicontinuous Aggregation and Sedimentation of Hybridoma Cells by Acoustic Resonance Fields," Biotechnology Progress, Mar. 1995, 11(2):146-152.
Rajendran et al., "Simulated moving bed chromatography for the separation of enantiomers," Journal of Chromatography A, Jan. 2009, 1216 (4):709-738.
Ransohoff, "The Potential for Continuous Chromatography and DSP in Clinical Manufacturing of Biopharmaceuticals," Biopharmaceutical Development & Production Week Conference, Huntington Beach, CA, Feb. 28, 2013, 29 pages.
Reuveny et al., "Comparison of cell propagation methods for their effect on monoclonal antibody yield in fermentors," Journal of Immunological Methods, Jan. 1986, 86(1):61-69.
Rey et al., "Glimpses into the Realm of Freeze-Drying: Classical Issues and New Ventures," Freeze Drying/Lyophilization of Pharmaceutical and Biological Products, 2010, pp. 1-28.
Riske et al., "The use of chitosan as a flocculant in mammalian cell culture dramatically improves clarification throughput without adversely impacting monoclonal antibody recovery," Journal of Biotechnology, Mar. 2007, 128 (4):813-823.
Rosa et al., "Application of aqueous two-phase systems to antibody purification: A multi-stage approach," Journal of Biotechnology, Feb. 2009, 139(4):306-313.

(56) References Cited

OTHER PUBLICATIONS

Rosa et al., "Aqueous two-phase systems: A viable platform in the manufacturing of biopharmaceuticals," Journal of Chromatography A, Apr. 2010, 1217(16):2296-2305.
Rosa et al., "Continuous aqueous two-phase extraction of human antibodies using a packed column," Journal of Chromatography B, Jan. 2012, 880:148-156.
Rosa et al., "Continuous purification of antibodies from cell culture supernatant with aqueous two-phase systems: From concept to process," Biotechnology Journal, Mar. 2013, 8(3):352-362.
Rosset et al., "Industrial application of preparative chromatography," Percolation Processes: Theory and Application, 1981, pp. 249-282.
Roth et al., "Using an external vortex flow filtration device for perfusion cell culture", Pharmaceutical Technology, Oct. 1997, 21(10):116-122.
Roush et al., "Advances in Primary Recovery: Centrifugation and Membrane Technology," Biotechnology Progress, 2008, 24(3):488-495.
Ruiz-Ruiz et al., "Aqueous two-phase affinity partitioning systems: Current applications and trends," Journal of Chromatography A, Jun. 2012, 1244:1-13.
Schmidt et al., "Crystallization for the Downstream Processing of Proteins". Engineering in Life Sciences, Jun. 2005, 5 (3):273-276.
Schwartz et al., "Introduction to Tangential Flow Filtration for Laboratory and Process Development Applications," dated Jan. 1, 2002, pp. 1-12, retrieved from the Internet: URL: http://separations.co.za/fileadmin/themes/default/pdf/2.%20PRODUCT%20LINES/R.%20PALL/ii.%20BIOPHARMACEUTICALS/Content%20Element%204/Minimate% 20System.pdf [retrieved on Oct. 20, 2017].
Seamans et al., "Kinetics of growth and antibody production by a hybridoma cell line in a perfusion culture," Journal of Fermentation and Bioengineering, 1990, 70(4):241-245.
Search Report and Written Opinion in Singapore Patent Application No. 10201803601S, dated Sep. 24, 2021, 10 pages.
Search Report and Written Opinion in Singapore Patent Application No. 10201804483P, dated May 11, 2022, 11 pages.
Searles et al., "Viable Cell Recycle with an Inclined Settler in the Perfusion Culture of Suspended Recombinant Chinese Hamster Ovary Cells," Biotechnology Progress, Mar. 1994, 10(2):198-206.
Sellin, "Partial Least Squares Analysis," International Journal of Educational Research, 1986, 10(2):189-200.
Shen et al., "CFD-aided cell settler design optimization and scale-up: Effect of geometric design and operational variables on separation performance," Biotechnology Progress, Apr. 2011, 27(5):1282-1296.
Shinkazh et al., "Countercurrent tangential chromatography for large-scale protein purification," Biotechnol Bioengineering, Mar. 2011, 108(3):582-591.
Office Action in Japanese Appln. No. 2019-508971, mailed on Jan. 25, 2022, 13 pages (with English translation).
Office Action in Japanese Appln. No. 2019-508971, mailed on Jun. 1, 2021, 13 pages (with English translation).
Office Action in Japanese Appln. No. 2020-035426, mailed on Apr. 6, 2021, 7 pages.
Office Action in Japanese Appln. No. 2020-070132, mailed on May 11, 2021, 14 pages.
Office Action in Japanese Appln. No. 2020-073759, mailed on May 18, 2021, 9 pages (with English translation).
Office Action in Japanese Appln. No. 2020-545704, mailed on Nov. 22, 2022, 6 pages (with English translation).
Office Action in Japanese Appln. No. 2021-510700, mailed on Dec. 10, 2024, 23 pages (with English translation).
Office Action in Japanese Appln. No. 2021-510700, mailed on Jul. 11, 2023, 5 pages (with English translation).
Office Action in Japanese Appln. No. 2021-510700, mailed on Mar. 14, 2023, 10 pages (with English translation).
Office Action in Japanese Appln. No. 2021-559051, mailed on Oct. 21, 2025, 6 pages (with English translation).
Office Action in Japanese Appln. No. 2022-082749, mailed on Jun. 13, 2023, 12 pages (with English translation).
Office Action in Japanese Appln. No. 2022-082749, mailed on Nov. 28, 2023, 11 pages (with English translation).
Office Action in Japanese Appln. No. 2023-017253, mailed on Apr. 23, 2025, 4 pages, (with English translation).
Office Action in Japanese Appln. No. 2023-017253, mailed on Jan. 14, 2025, 4 pages, (with English translation).
Office Action in Japanese Appln. No. 2023-017253, mailed on Jan. 16, 2024, 7 pages (with English translation).
Office Action in Japanese Appln. No. 2023-191994, mailed on Nov. 11, 2025, 6 pages (with English translation).
Office Action in Japanese Appln. No. 2024-172864, mailed on Oct. 21, 2025, 6 pages (with English translation).
Office Action in Korean Appln No. 10-2020-7027993, mailed on Nov. 29, 2023, 11 pages.
Office Action in Korean Appln. No. 10-2015-7027532, mailed on Aug. 5, 2020, 12 pages.
Office Action in Korean Appln. No. 10-2015-7027532, mailed on Feb. 22, 2021, 11 pages.
Office Action in Korean Appln. No. 10-2016-7009570, mailed on Aug. 30, 2021, 5 pages (with English translation).
Office Action in Korean Appln. No. 10-2016-7009570, mailed on Feb. 19, 2021, 30 pages (with English translation).
Office Action in Korean Appln. No. 10-2016-7009570, mailed on Nov. 24, 2021, 6 pages (with English translation).
Office Action in Korean Appln. No. 10-2016-7022274, mailed on Jan. 25, 2021, 12 pages.
Office Action in Korean Appln. No. 10-2016-7022274, mailed on Jul. 5, 2021, 6 pages (with English translation).
Office Action in Korean Appln. No. 10-2017-7013748, mailed on Feb. 9, 2022, 15 pages (with English translation).
Office Action in Korean Appln. No. 10-2019-7007518, mailed on Mar. 29, 2022, 8 pages (with English translation).
Office Action in Korean Appln. No. 10-2021-7009242, mailed on Jul. 23, 2024, 22 pages (with English translation).
Office Action in Korean Appln. No. 10-2021-7035567, mailed on Aug. 21, 2025, 8 pages (with English translation).
Office Action in Korean Appln. No. 10-2022-7006373, mailed on Jan. 30, 2023, 6 pages (with English translation).
Office Action in Korean Appln. No. 10-2022-7006373, mailed on Jun. 20, 2022, 15 pages (with English translation).
Office Action in Korean Appln. No. 10-2022-7006373, mailed on Jun. 29, 2023, 5 pages (with English translation).
Office Action in Korean Appln. No. 10-2022-7006373, mailed on Sep. 24, 2024, 43 pages (with English translation).
Office Action in Korean Appln. No. 10-2023-7033339, mailed on Oct. 25, 2024, 4 pages (with English abstract).
Office Action in Mexican Appln. No. MX/a/2015/012114, mailed on Oct. 3, 2019, 2 pages.
Office Action in Mexican Appln. No. MX/a/2016/003440, mailed on Aug. 6, 2019, 4 pages (with English translation).
Office Action in Mexican Appln. No. MX/a/2016/003440, mailed on Mar. 2, 2021, 6 pages (with English translation).
Office Action in Mexican Appln. No. MX/a/2016/003440, mailed on Mar. 3, 2020, 11 pages (with English translation).
Office Action in Mexican Appln. No. MX/a/2016/003440, mailed on Oct. 1, 2020, 10 pages (with English translation).
Office Action in Mexican Appln. No. MX/a/2016/009295, mailed on Aug. 20, 2020, 1 page.
Office Action in Mexican Appln. No. MX/a/2016/009295, mailed on Feb. 26, 2020, 3 pages.
Office Action in Mexican Appln. No. MX/a/2016/009296, mailed on Jun. 17, 2019, 2 pages.
Office Action in Mexican Appln. No. MX/a/2016/009296, mailed on Sep. 30, 2019, 3 pages.
Office Action in Mexican Appln. No. MX/a/2017/005348, mailed on Oct. 24, 2022, 3 pages.
Office Action in Mexican Appln. No. MX/A/2019/001859, mailed on Aug. 6, 2021, 9 pages (with English translation).
Office Action in Mexican Appln. No. MX/a/2019/001859, mailed on Feb. 25, 2021, 9 pages (with English translation).

(56) References Cited

OTHER PUBLICATIONS

Office Action in Mexican Appln. No. MX/a/2019/001859, mailed on Jan. 27, 2022, 13 pages (with English summary).
Office Action in Mexican Appln. No. MX/a/2019/001859, mailed on Jul. 25, 2022, 11 pages (with English summary).
Office Action in Mexican Appln. No. MX/a/2019/014428, mailed on Aug. 4, 2020, 5 pages.
Office Action in Japanese Appln. No. 2023-017253, mailed on Jul. 16, 2024, 6 pages, (with English translation).
Office Action in Russian Appln. No. 2015142657, mailed on Jan. 11, 2018, 2 pages.
Office Action in Taiwanese Appln. No. 109107478, mailed on Jun. 1, 2022, 5 pages (with English summary).
Second Third-Party submission under 37 CFR 1.290 and Concise Description of the Relevance filed in U.S. Appl. No. 14/598,401, dated Nov. 2, 2015, 21 pages.
Third-Party Submission under 37 CFR 1.290 and Concise Description of Relevance filed in U.S. Appl. No. 14/598,450, filed Nov. 2, 2015, 12 pages.
Third-Party Submission under 37 CFR 1.290 and Concise Description of Relevance filed in U.S. Appl. No. 14/598,450, filed Nov. 5, 2015, 21 pages.
Third-Party Submission under 37 CFR 1.290 and Concise Description of the Relevance filed in U.S. Appl. No. 14/598,401, filed Dec. 3, 2015, 16 pages.
Office Action in U.S. Appl. No. 14/627,559, mailed on Feb. 18, 2016, 17 pages.
Office Action in U.S. Appl. No. 17/643, 128, mailed on Sep. 9, 2022, 13 pages.
Office Action in Australian Appln. No. 2022221495, mailed on Aug. 23, 2024, 4 pages.
Office Action in Australian Appln. No. 2022221495, mailed on Mar. 21, 2024, 4 pages.
Office Action in Australian Appln. No. 2022221495, mailed on Sep. 8, 2023, 4 pages.
Office Action in Australian Appln. No. 2024219335, mailed on Jul. 29, 2025, 4 pages.
Office Action in Brazilian Appln. No. 112016005545-4, mailed on Nov. 3, 2020, 8 pages (with English translation).
Office Action in Brazilian Appln. No. 112016005545-4, mailed on Oct. 8, 2019, 5 pages (with English translation).
Office Action in Brazilian Appln. No. BR112015021495-9, mailed on Apr. 10, 2023, 7 pages (English translation only).
Office Action in Brazilian Appln. No. BR112015021495-9, mailed on Apr. 16, 2024, 6 pages (English translation only).
Office Action in Brazilian Appln. No. BR112015021495-9, mailed on May 22, 2020, 7 pages (with English translation).
Office Action in Brazilian Appln. No. BR112015021495-9, mailed on Nov. 28, 2022, 10 pages (with English translation).
Office Action in Brazilian Appln. No. BR112016016329-0, mailed on May 22, 2020, 5 pages.
Office Action in Brazilian Appln. No. BR112016016329-0, mailed on May 31, 2023, 7 pages (with English translation).
Office Action in Brazilian Appln. No. BR112016016332-0, mailed on Dec. 21, 2021, 4 pages (English translation only).
Office Action in Brazilian Appln. No. BR112016016332-0, mailed on Dec. 26, 2019, 5 pages.
Office Action in Brazilian Appln. No. BR112017008252-7, mailed on Aug. 3, 2021, 10 pages (with English translation).
Office Action in Brazilian Appln. No. BR112017008252-7, mailed on Nov. 12, 2019, 9 pages.
Office Action in Brazilian Appln. No. BR112019003013-1, mailed on Sep. 20, 2022, 5 pages (with English translation).
Office Action in Brazilian Appln. No. BR112020017726-1, mailed on Aug. 23, 2022, 5 pages (with English translation).
Office Action in Brazilian Appln. No. BR112020017726-1, mailed on May 18, 2023, 8 pages (with English translation).
Office Action in Brazilian Appln. No. BR112021003420-0, mailed on May 13, 2025, 16 pages (with English translation).
Office Action in Brazilian Appln. No. BR112021003420-0, mailed on May 23, 2023, 5 pages (with English translation).
Office Action in Brazilian Appln. No. BR112021003420-0, mailed on Oct. 30, 2025, 6 pages (with English translation).
Office Action in Brazilian Appln. No. BR122021001466-3, mailed on Apr. 13, 2021, 7 pages (with English translation).
Office Action in Brazilian Appln. No. BR122021005691-9, mailed on May 4, 2023, 10 pages (with English translation).
Office Action in Brazilian Appln. No. BR122021005691-9, mailed on Nov. 28, 2022, 12 pages (with English translation).
Office Action in Brazilian Appln. No. BR122022005877-9, mailed on Jul. 29, 2022, 8 pages (with English translation).
Office Action in Brazilian Appln. No. BR122022005877-9, mailed on Mar. 6, 2023, 5 pages (with English translation).
Office Action in Brazilian Appln. No. BR122022005877-9, mailed on May 19, 2022, 9 pages.
Office Action in Brazilian Appln. No. BR122024015143-0, mailed on Jan. 24, 2026, 10 pages (with English translation).
Office Action in Brazilian Appln. No. BR122024015143-0, mailed on May 14, 2025, 17 pages (with English translation).
Office Action in Canadian Appln. No. 2,902,854, mailed on Aug. 25, 2021, 3 pages.
Office Action in Canadian Appln. No. 2,902,854, mailed on Jun. 27, 2022, 3 pages.
Office Action in Canadian Appln. No. 2,902,854, mailed on Nov. 18, 2019, 4 pages.
Office Action in Canadian Appln. No. 2,902,854, mailed on Oct. 5, 2020, 4 pages.
Office Action in Canadian Appln. No. 2,924,332, mailed on Jul. 30, 2020, 2 pages.
Office Action in Canadian Appln. No. 2,924,332, mailed on Jul. 9, 2021, 3 pages.
Office Action in Canadian Appln. No. 2,936,951, mailed on Dec. 22, 2020, 4 pages.
Office Action in Canadian Appln. No. 2,936,951, mailed on Nov. 15, 2021, 3 pages.
Office Action in Canadian Appln. No. 2,936,969, mailed on Apr. 1, 2021, 4 pages.
Office Action in Canadian Appln. No. 2,936,969, mailed on Sep. 21, 2021, 3 pages.
Chang, "Continuous fractionation of human plasma proteins by precipitation from the suspension of the recycling stream," Biotechnology and Bioengineering, May 1988, 31(8):841-846.
Chase, "Purification of proteins by adsorption chromatography in expanded beds," Trends in Biotechnology, Aug. 1994, 12(8):296-303.
Chatfield et al., "Principal component analysis," Introduction to Multivariate Analysis, Springer, 1980, pp. 57-81.
Chhatre et al., "A decision-support model for evaluating changes in biopharmaceutical manufacturing processes," Bioprocess and Biosystems Engineering, Nov. 2006, 30(1):1-11.
Chisti et al., "Large Scale Protein Separations: Engineering Aspects of Chromatography," Biotechnology Advances, Jan. 1990, 8:699-708.
Chotteau et al., "Perfusion Processes," Animal Cell Culture, Nov. 2014, pp. 407-443.
Chromatographyonline.com [online], "The LCGC Blog: So Just How Well Set-Up is Your UV Detector?," Sep. 17, 2014, retrieved on Sep. 3, 2025, retrieved from URL <https://www.chromatographyonline.com/view/lcgc-blog-so-just-how-well-set-your-uv-detector>, 13 pages.
Clincke et al., "Study of a recombinant CHO cell line producing a monoclonal antibody by ATF or TFF external filter perfusion in a WAVE BioreactorTM," BMC Proceedings, 2011, 5(Suppl 8):P105.
Clincke et al., "Very High Density of Chinese Hamster Ovary Cells in Perfusion by Alternating tangential Flow or Tangential Flow Filtration in WAVE BioreactorTM—Part II: Applications for Antibody Production and Cryopreservation," Biotechnol. Prog., 2013, 29(3):768-777.
Clincke et al., "Very High Density of Chinese Hamster Ovary Cells in Perfusion by Alternating tangential Flow or Tangential Flow Filtration in WAVE BioreactorTM. Part I. Effect of the Cell Density on the Process," Biotechnol. Prog., 2013, 29(3):754-767.

(56) References Cited

OTHER PUBLICATIONS

Communication in European Appln. No. 14714835.7, dated Mar. 23, 2018, 4 pages.
Communication in European Appln. No. 14780959.4, dated Jun. 19, 2017, 5 pages.
Communication in European Appln. No. 14780959.4, dated Sep. 25, 2017, 4 pages.
Communication in European Appln. No. 15702074.4, dated Dec. 18, 2019, 23 pages.
Communication in European Appln. No. 15708622.4, dated Dec. 11, 2017, 3 pages.
Communication in European Appln. No. 15708622.4, dated Jul. 2, 2019, 2 pages.
Communication in European Appln. No. 15708622.4, dated Nov. 26, 2018, 3 pages.
Communication in European Appln. No. 15791822.8, dated May 8, 2018, 4 pages.
Communication in Opposition against European Appln. No. 14780959.4, dated Jan. 12, 2023, 56 pages.
Crowley et al., "Using sound waves for cGMP manufacturing of a fusion protein with mammalian cells," BioProcess International, 2004, 2(3):46-50.
Cytiva.com [online], "ReadyToProcessTM - hollow fiber cartridges," Cytiva, 2020-2021, 6 pages.
Dalm et al., "Effect of feed and bleed rate on hybridoma cells in an acoustic perfusion bioreactor: Part I. Cell density, viability, and cell-cycle distribution," Biotechnology and Bioengineering, Sep. 2004, 88(5):547-557.
Dalwadi et al., "Comparison of Diafiltration and Tangential Flow Filtration for Purification of Nanoparticle Suspensions," Pharmaceutical Research, Dec 1, 2005, 22(12):2152-2162.
De la Broise et al., "Long-term perfusion culture of hybridoma: A "grow or die" cell cycle system," Biotechnology and Bioengineering, Oct. 1991, 38(7):781-787.
De Meyer et al., "Evaluation of spin freezing versus conventional freezing as part of a continuous pharmaceutical freeze-drying concept for unit doses," International Journal of Pharmaceutics, Dec 2015, 496(1):75-85.
Degenhardt et al., "Separation and purification of anthocyanins by high-speed countercurrent chromatography and screening for antioxidant activity," Journal of Agricultural and Food Chemistry, Feb. 21, 2000, 48(2):338-343.
Deo et al., "Practical Considerations in Operation and Scale-up of Spin-Filter Based Bioreactors for Monoclonal Antibody Production," Biotechnology Progress, 1996, 12(1):57-64.
Doblhoff-Dier et al., "A Novel Ultrasonic Resonance Field Device for the Retention of Animal Cells," Biotechnology Progress, 1994, 10(4):428-432.
Dutta et al., "Performance optimization of continuous countercurrent tangential chromatography for antibody capture," Biotechnology Progress, Feb. 2016, 32(2):430-439.
Dutta et al., "Purification of monoclonal antibodies from clarified cell culture fluid using Protein A capture continuous countercurrent tangential chromatography," Journal of Biotechnology, Nov. 2015, 213:54-64.
Eggersgluess et al., "Multi-Stage Aqueous Two-Phase Extraction for the Purification of Monoclonal Antibodies," Chemical Engineering & Technology, Feb. 2014, 37(4):675-682.
Elsayed et al., "Application of hydrocyclones for continuous cultivation of SP-2/0 cells in perfusion bioreactors: Effect of hydrocyclone operating pressure," BMC Proceedings, Nov. 2011, 5(Supp. 8):p65.
Elsayed et al., "The Potential of Hydrocyclone Application for Mammalian Cell Separation in Perfusion Cultivation Bioreactors," International Journal of Biotechnology for Wellness Industries, Dec 2013, 2(4):153-163.
Elsayed et al., "Use of Hydrocyclones for Mammalian Cell Retention: Separation Efficiency and Cell Viability (Part 1)," Engineering in Life Sciences, Sep. 2006, 6(4):347-354.
Emery et al., "Oxygenation of intensive cell-culture system," Applied Microbiology and Biotechnology, Nov. 1995, 43(6):1028-1033.
Espitia-Saloma et al., "An integrated practical implementation of continuous aqueous two-phase systems for the recovery of human IgG: From the microdevice to a multistage bench-scale mixer-settler device," Biotechnology Journal, Feb. 2016, 11(5):708-716.
Espitia-Saloma et al., "Continuous aqueous two-phase systems devices for the recovery of biological products, " Food and Bioproducts Processing, Apr. 2014, 92(2):101-112.
European Communication in Appln. No. 17762255.2, dated Apr. 5, 2019, 2 pages.
European Communication in Appln. No. 17762255.2, dated Jun. 22, 2020, 4 pages.
European Search Report in Appln. No. 21193609.1, dated Dec. 21, 2021, 9 pages.
European Third-Party Observations in Appln. No. 15702074.4, dated May 3, 2021, 4 pages.
Examination Report in Singapore Appln. No. 11201703265X, dated Jan. 12, 2018, 4 pages.
Farid, "Process economics of industrial monoclonal antibody manufacture," Journal of Chromatography B, Mar. 2007, 848(1):8-18.
Ferre et al., "Purification of correctly oxidized MHC class I heavy-chain molecules under denaturing conditions: A novel strategy exploiting disulfide assisted protein folding," Protein Science, Mar. 12, 2003, 12(3):551-559.
Feuser et al., "Interaction of mammalian cell culture broth with adsorbents in expanded bed adsorption of monoclonal antibodies," Process Biochemistry, Feb. 1999, 34(2): 159-165.
First Third-Party Submission under 37 CFR 1.290 and Concise Description of Relevance filed in U.S. Appl. No. 14/598,401, dated Nov. 2, 2015, 16 pages.
Flickinger et al., "Encyclopedia of Bioprocess Technology: Fermentation, Biocatalysis, and Bioseparation," A Wiley-Interscience Publication, 1999, pp. 1695-1705.
Office Action in Mexican Appln. No. MX/a/2019/014428, mailed on Jan. 28, 2021, 5 pages.
Office Action in Mexican Appln. No. MX/a/2020/001823, mailed on Apr. 14, 2025, 10 pages (with English translation).
Office Action in Mexican Appln. No. MX/a/2020/001823, mailed on Aug. 5, 2024, 8 pages (with English translation).
Office Action in Mexican Appln. No. MX/a/2020/009133, mailed on May 20, 2025, 26 pages (with English translation).
Office Action in Mexican Appln. No. MX/a/2021/002314, mailed on Jul. 14, 2025, 14 pages (with English translation).
Office Action in Mexican Appln. No. MX/a/2021/007792, mailed on Aug. 14, 2024, 20 pages (with English translation).
Office Action in Mexican Appln. No. MX/a/2021/007792, mailed on Jan. 31, 2025, 13 pages (with English translation).
Office Action in Russian Appln. No. 2015142657, mailed on Apr. 18, 2018, 10 pages.
Office Action in Russian Appln. No. 2015142657, mailed on Aug. 4, 2017, 14 pages.
Office Action in Russian Appln. No. 2015142657, mailed on Dec. 22, 2017, 8 pages.
Office Action in Russian Appln. No. 2016133483, mailed on Aug. 20, 2018, 14 pages.
Office Action in Russian Appln. No. 2016133484, mailed on Aug. 22, 2018, 8 pages.
Office Action in Russian Appln. No. 2017115655, mailed on Apr. 17, 2019, 7 pages.
Office Action in Russian Appln. No. 2017115655, mailed on Aug. 7, 2019, 19 pages.
Office Action in Russian Appln. No. 2017115655, mailed on Jul. 15, 2019, 6 pages (with English translation).
Office Action in Russian Appln. No. 2017115655, mailed on Nov. 25, 2019, 15 pages (with English translation).
Office Action in Russian Appln. No. 2018122100, mailed on Aug. 6, 2021, 15 pages (with English translation).
Office Action in Russian Appln. No. 2019102195, mailed on Jun. 22, 2022, 10 pages (with English translation).
Office Action in Russian Appln. No. 2019102196, mailed on Apr. 4, 2023, 7 pages (with English translation).
Office Action in Russian Appln. No. 2019102196, mailed on Jun. 22, 2022, 10 pages (with English translation).

(56) References Cited

OTHER PUBLICATIONS

Office Action in Russian Appln. No. 2019102196, mailed on Nov. 11, 2022, 7 pages (with English translation).
Office Action in Russian Appln. No. 2019107142, mailed on Dec. 17, 2020, 18 pages (with English translation).
Office Action in Russian Appln. No. 2019107142, mailed on May 4, 2021, 19 pages (with English translation).
Office Action in Russian Appln. No. 2020102925, mailed on Aug. 12, 2022, 5 pages (with English translation).
Office Action in Russian Appln. No. 2020102925, mailed on Feb. 16, 2022, 16 pages (with English translation).
Office Action in Russian Appln. No. 2020132277, mailed on Oct. 17, 2022, 19 pages (with English translation).
Office Action in Russian Appln. No. 2021108240, mailed on Jan. 26, 2023, 24 pages (with English translation).
Office Action in Russian Appln. No. 2021108240, mailed on May 18, 2023, 12 pages (with English translation).
Office Action in Singapore Appln. No. 10201709131U, mailed on Dec. 1, 2023, 8 pages.
Office Action in Singapore Appln. No. 11202008436V, mailed on Jan. 10, 2022, 4 pages.
Office Action in Singapore Appln. No. 11202008436V, mailed on Jun. 15, 2023, 7 pages.
Office Action in Taiwanese Appln. No. 103107864, mailed on Sep. 11, 2018, 1 page.
Office Action in Taiwanese Appln. No. 104101335, mailed on Jan. 19, 2019, 1 page.
Office Action in Taiwanese Appln. No. 104134623, mailed on Dec. 16, 2019, 2 pages (with English translation).
Office Action in Taiwanese Appln. No. 104134623, mailed on Jan. 10, 2019, 3 pages (with English translation).
Office Action in Taiwanese Appln. No. 104134623, mailed on Jul. 17, 2019, 1 page (with English translation).
Office Action in Taiwanese Appln. No. 106127646, mailed on Sep. 6, 2021, 3 pages (English translation only).
Office Action in Taiwanese Appln. No. 108105550, mailed on Feb. 10, 2020, 1 page.
Office Action in Taiwanese Appln. No. 108107091, mailed on Apr. 26, 2023, 43 pages (with English translation).

* cited by examiner

CONTINUOUS PRODUCTION OF RECOMBINANT PROTEINS

This application is a divisional application of U.S. Non-Provisional application Ser. No. 16/837,126, filed Apr. 1, 2020, which claims the benefit of U.S. Provisional Application No. 62/828,755, filed Apr. 3, 2019, the disclosure of each of which is explicitly incorporated by reference herein.

FIELD OF THE DISCLOSURE

The present disclosure relates to methods and systems for the continuous production of recombinant proteins. In particular embodiments, the disclosure relates to methods and systems using capture chromatography, post-capture chromatography, virus filtration, and ultrafiltration/diafiltration for the continuous production of recombinant proteins.

BACKGROUND

Continuous manufacturing is a routine way of production for industries such as petrochemical and food production. Benefits of a continuous process include steady state operation, reduced equipment size, high-volumetric productivity, streamlined process flow, low-cycle times, and reduced capital cost. Konstantinov et al., *J. Pharm. Sci.* 104(3): 813-20 (2015).

Continuous manufacturing has not been widely implemented in the biopharmaceutical industry. Because technological needs for upstream and downstream development are rather different, the experience with continuous downstream operations is limited. Thus, there remains a need for integrated continuous bioprocesses that can be run for extended periods of time with minimal operator interaction for the biopharmaceutical industry.

SUMMARY

Provided herein is a continuous method for producing a recombinant protein, the method comprising: (a) capturing the recombinant protein from a substantially cell-free sample using one or a plurality of capture chromatography systems and eluting the recombinant protein from the one or plurality of capture chromatography systems to produce eluates comprising the recombinant protein, wherein a single or multiple eluates are homogenized into a single mixture comprising the recombinant protein, (b) subjecting the single mixture to one or a plurality of post-capture chromatography systems and collecting product output comprising the recombinant protein, and (c) subjecting the product output to ultrafiltration and diafiltration to purify the recombinant protein, wherein the method is integrated and continuous from step (a) to step (c).

Also provided herein is a manufacturing system for producing a recombinant protein, the manufacturing system comprising: (a) a first unit operation comprising a bioreactor comprising host cells that produce the recombinant protein, (b) a second unit operation comprising one or a plurality of capture chromatography systems, (c) a third unit operation comprising one or a plurality of post-capture chromatography systems, and (d) a fourth unit operation comprising an ultrafiltration system and diafiltration system.

Also provided herein is a continuous method for producing a recombinant protein, the method comprising: (a) capturing the recombinant protein from a substantially cell-free sample using one or a plurality of capture chromatography systems and eluting the recombinant protein from the one or plurality of capture chromatography systems to produce eluates comprising the recombinant protein, wherein the eluates are homogenized into a single mixture comprising the recombinant protein, (b) subjecting the homogenized single mixture to virus inactivation, (c) subjecting the homogenized single mixture from step (b) to one or a plurality of post-capture chromatography systems and collecting product output comprising the recombinant protein, (d) subjecting the product output of step to virus filtration, and (e) subjecting the product output from step (d) to ultrafiltration and diafiltration to purify the recombinant protein, wherein the method is integrated and continuous from step (a) to step (e).

Other aspects, embodiments, and implementations will become apparent from the following detailed description and claims, with reference, where appropriate, to the accompanying drawings.

BRIEF DESCRIPTION OF THE DRAWINGS

FIG. 2A shows the unit operation integration durations for continuous operation for each operation unit. FIG. 2B shows the average protein residence time for each unit operation. The methods and systems disclosed herein generated ~5 kg drug substance over a 25-day period.

FIG. 3A shows Protein A eluate concentrations (g/L), FIG. 3B shows Protein A eluate residual host cell proteins, FIG. 3C shows Protein A eluate residual Protein, FIG. 3D shows Protein A inlet mass flow, and FIGS. 3E and 3F show Protein A ultraviolet chromatogram.

FIG. 4A shows the viral inactivation pH maintained throughout the unit operation, FIG. 4B shows protein concentration prior to inactivation, FIG. 4C shows protein mass flow during viral inactivation, FIG. 4D shows acid flow during viral inactivation, FIG. 4E shows base flow during viral inactivation, FIG. 4F shows high molecular weight species during viral inactivation, and FIG. 4G shows protein concentration following viral inactivation.

FIG. 5A shows post-capture eluate residual Protein A, FIG. 5B shows post-capture eluate protein concentration, FIG. 5C shows ultraviolet chromatogram, and FIG. 5D show post-capture eluate residual host cell protein.

FIG. 6B shows protein concentration following viral filtration, FIG. 6C shows high molecular weight species following viral filtration, FIG. 6D shows protein mass flux during viral filtration, FIG. 6E shows filtrate volume flux during virus filtration, FIG. 6F shows transmembrane pressure during viral filtration, and FIG. 6G shows filter performance during viral filtration.

FIG. 7A shows protein concentration and conversion following ultrafiltration, FIG. 7B shows filter performance during ultrafiltration, FIG. 7C shows inlet protein mass flux during ultrafiltration, FIG. 7D shows permeate volume flux during ultrafiltration, and FIG. 7E shows transmembrane pressure during ultrafiltration.

FIG. 8A shows permeate volume flux during diafiltration, FIG. 8B shows protein mass flux during diafiltration, FIG. 8C shows transmembrane pressure during diafiltration, FIG. 8D shows diafiltration ratio, and FIG. 8E shows filter performance during diafiltration.

FIG. 9A shows the concertation of the drug substance, FIG. 9B shows high molecular weight species of the drug substance, FIG. 9C shows the charge profile of the drug substance, FIG. 9D shows the osmolality of the drug substance, FIG. 9E shows the pH of the drug substance, FIG. 9F shows host cell protein as measured by ELISA for the drug substance, FIG. 9G shows the non-reduced purity of the drug substance, and FIG. 9H shows the residual Protein A of the drug substance.

DETAILED DESCRIPTION

Figure 1:
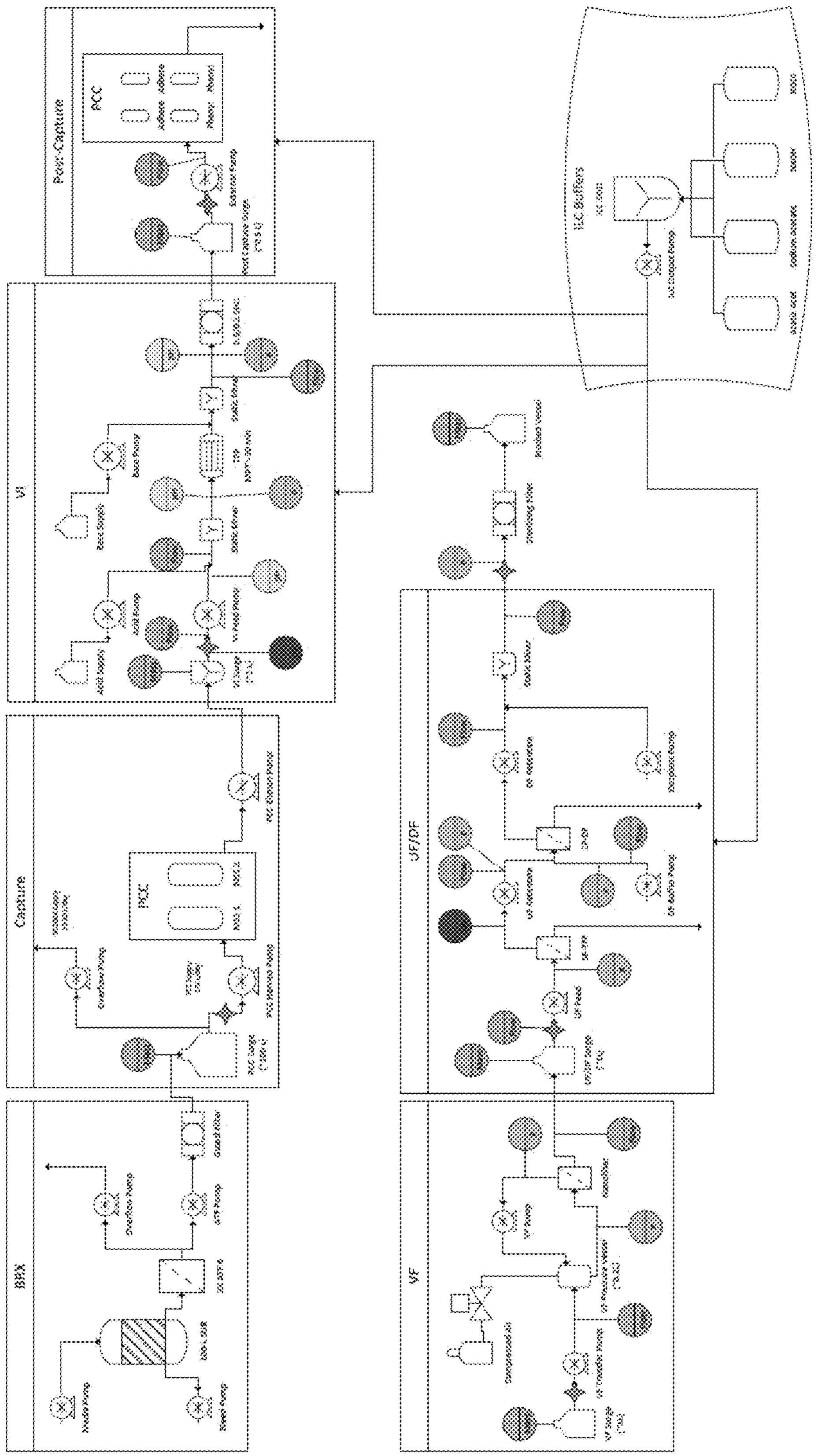
FIG. 1 is a schematic illustrating the process flow of the methods disclosed herein. The process flow includes a continuous process for production of a recombinant protein using in-line buffers comprising: (1) production of the recombinant protein in a bioreactor coupled with dual Alternating Tangential Flow (ATF) filters and cell separation (labeled as "BRX"), (2) capture of the recombinant protein using one or plurality of capture chromatography systems to capture the recombinant protein present in the culture medium obtained from the bioreactor connected to the capture chromatography system (labeled as "Capture"), (3) viral inactivation of the medium (labeled as "VI"), (4) subjecting the medium to one or a plurality of post-capture chromatography systems (labeled as "Post-Capture"), (5) viral filtration of the medium, and (6) ultrafiltration/diafiltration of the medium.
Figure 2B:
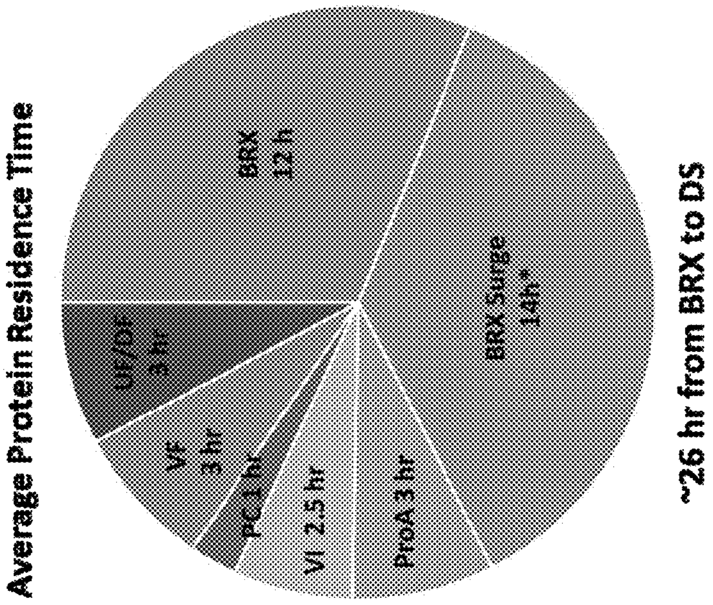
FIGS. 2A and 2B show an overview of the unit operation integration of the methods and systems disclosed herein.
Figure 2A:
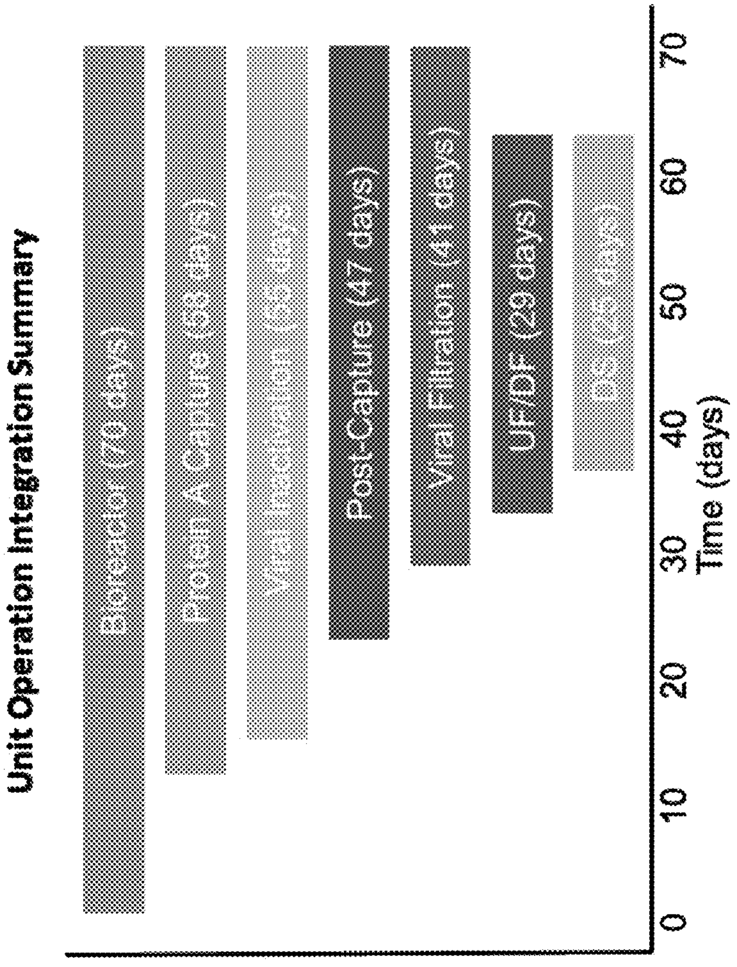
Figure 3A:
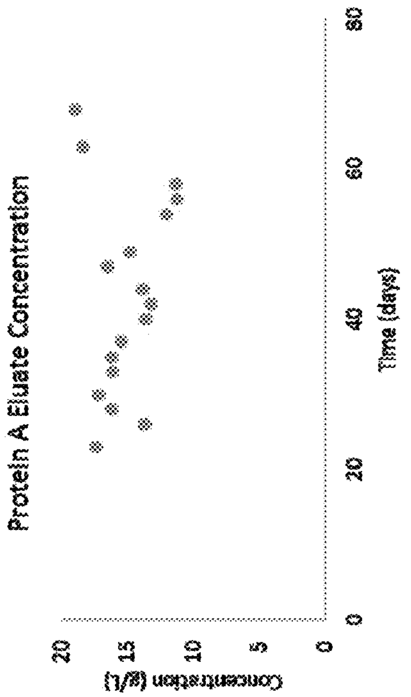
FIGS. 3A-3F are graphs showing Protein A operation performance for the methods and systems disclosed herein.
Figure 3B:
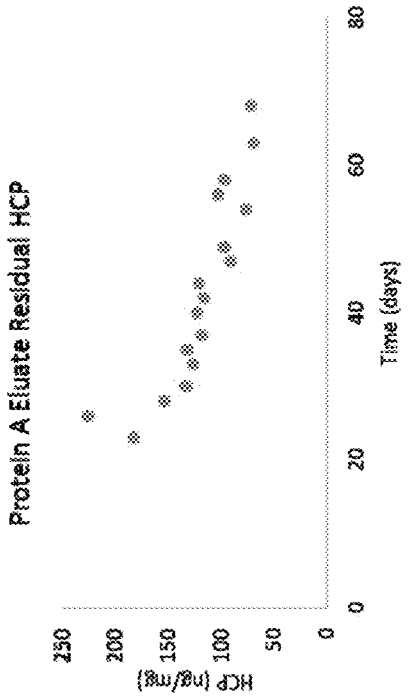
Figure 3C:
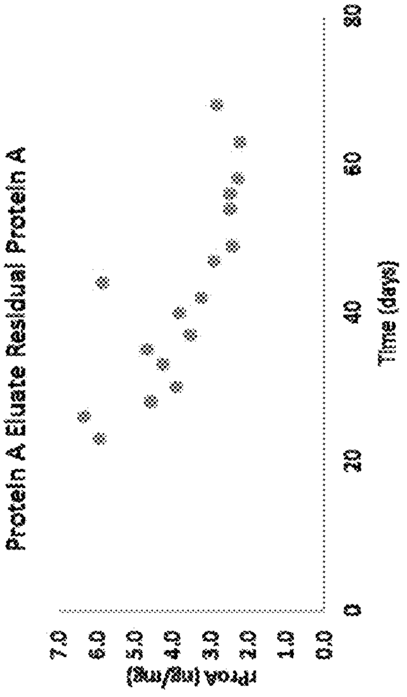
Figure 3D:
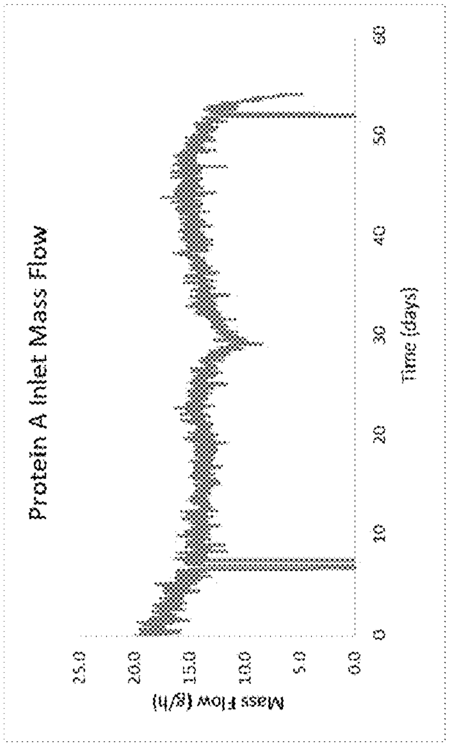
Figure 3F:
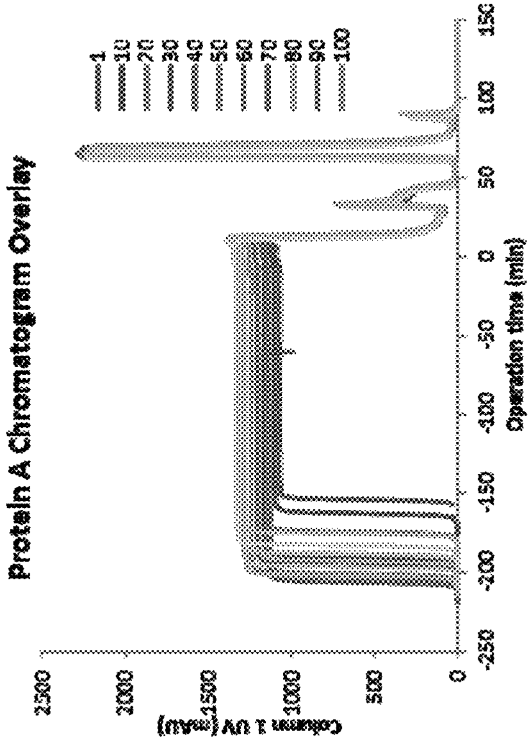
Figure 3E:
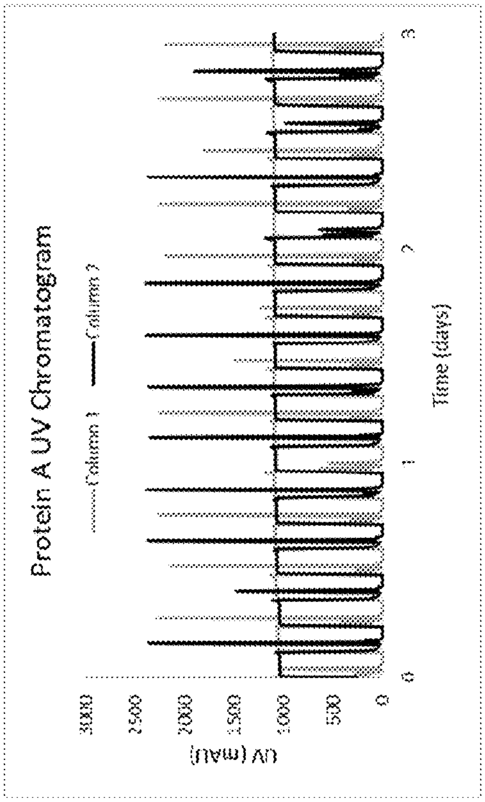
Figure 4A:
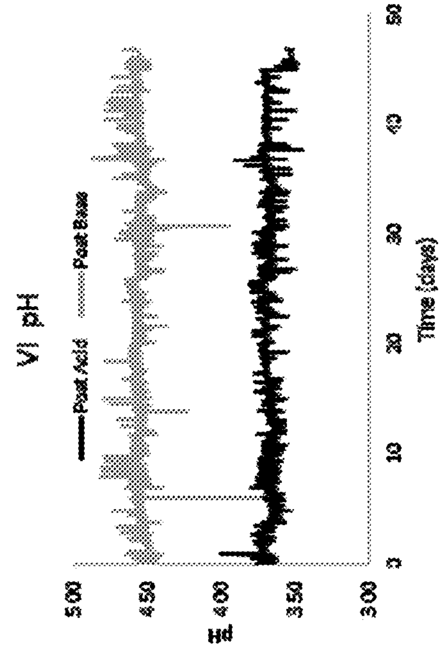
FIGS. 4A-4G are graphs showing viral inactivation operation performance for the methods and systems disclosed herein.
Figure 4B:
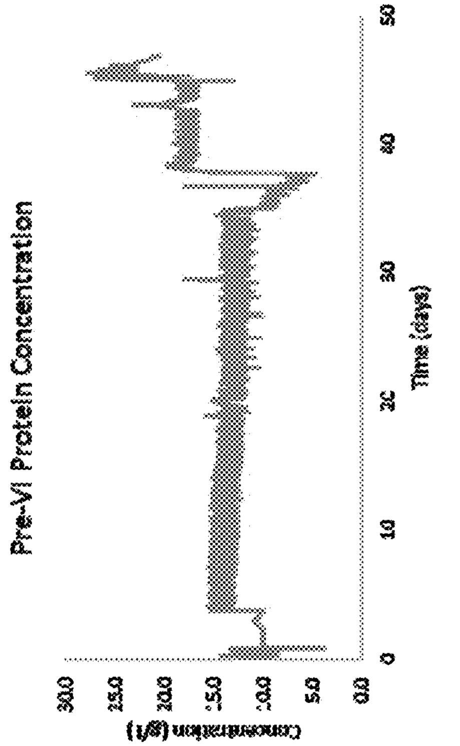
Figure 4D:
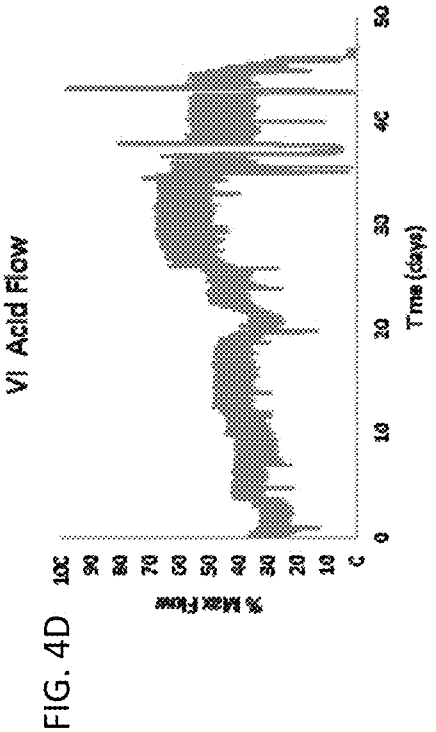
Figure 4C:
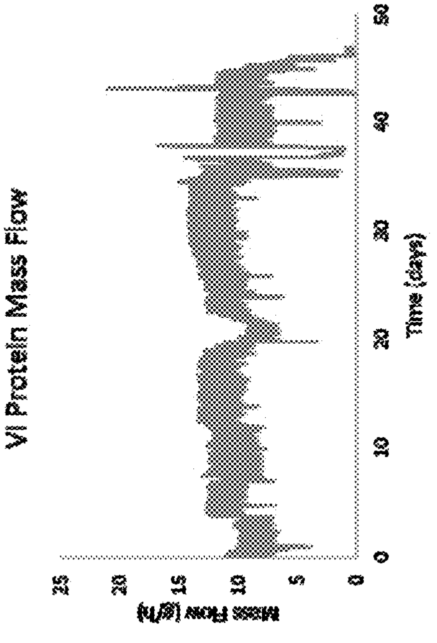
Figure 4E:
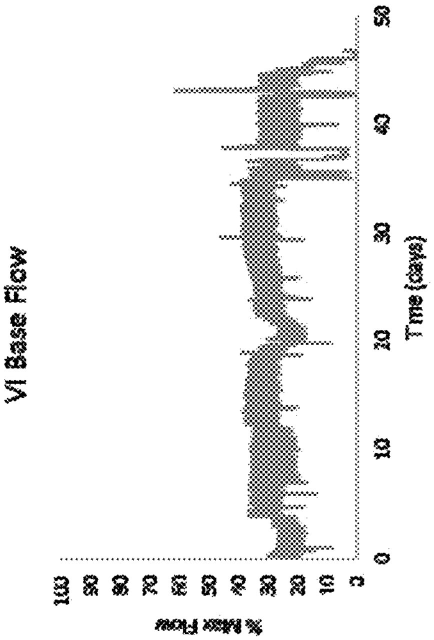
Figure 4F:
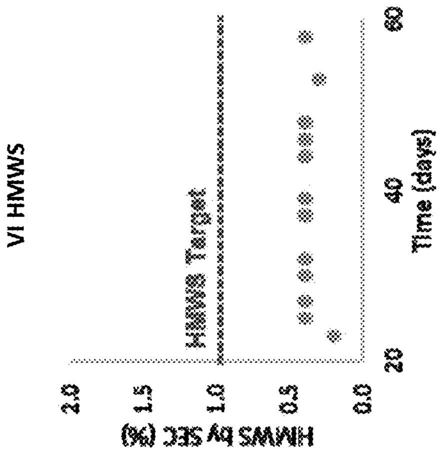
Figure 4G:
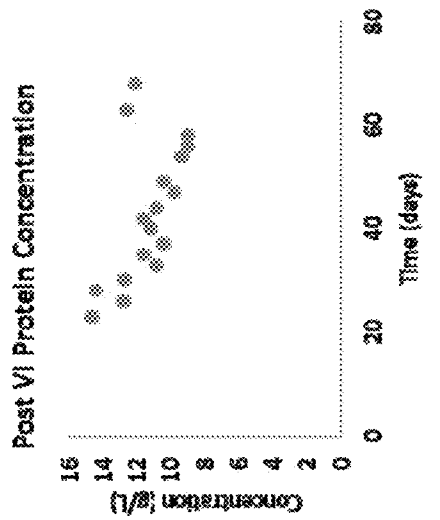
Figure 5B:
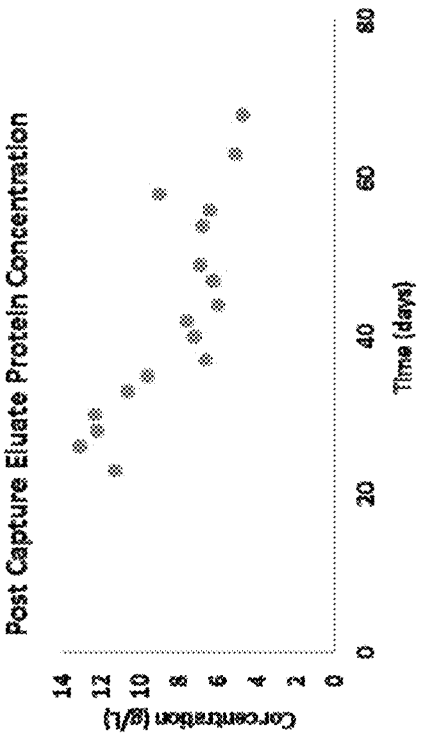
FIGS. 5A-5D are graphs showing post-capture operation performance for the methods and systems disclosed herein.
Figure 5A:
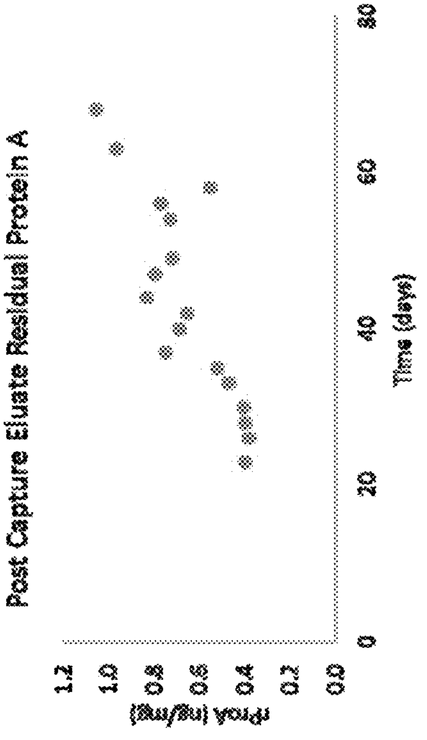
Figure 5C:
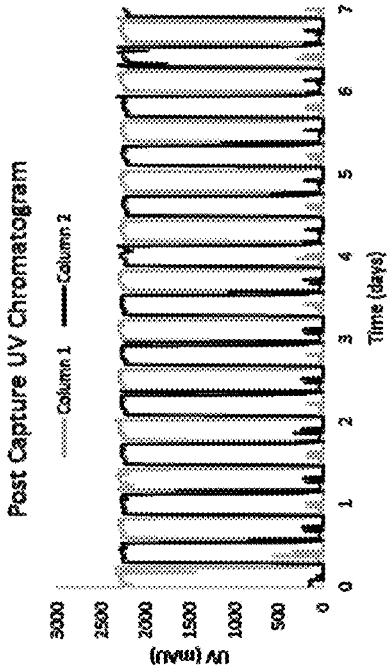
Figure 5D:
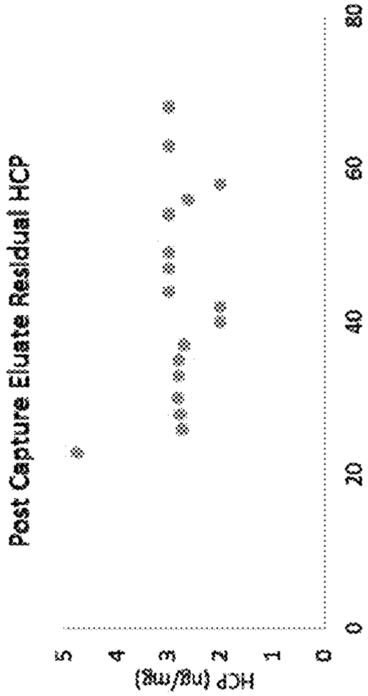

The present disclosure relates to methods and systems for the continuous production of recombinant proteins. In particular embodiments, the disclosure relates to methods and systems using capture chromatography, post-capture chromatography, and ultrafiltration/diafiltration for the production of recombinant proteins. The methods and systems described herein provide for the continuous and time-efficient production of a recombinant protein.

As utilized in accordance with the present disclosure, unless otherwise indicated, all technical and scientific terms shall be understood to have the same meaning as commonly understood by one of ordinary skill in the art. Unless otherwise required by context, singular terms shall include pluralities and plural terms shall include the singular.

In some embodiments provided herein is a continuous method for producing a recombinant protein, the method comprising capturing the recombinant protein from a substantially cell-free sample using one or a plurality of capture chromatography systems and eluting the recombinant protein from the one or plurality of capture chromatography systems to produce eluates comprising the recombinant protein, wherein the eluates are homogenized into a single mixture comprising the recombinant protein, subjecting the homogenized single mixture to one or a plurality of post-capture chromatography systems and collecting product output comprising the recombinant protein, and subjecting the product output to ultrafiltration and diafiltration to purify the recombinant protein, wherein the method is integrated and runs continuously.

Also provided herein is a manufacturing system for producing a recombinant protein, the manufacturing system comprising a first operation unit comprising a bioreactor comprising host cells that produce the recombinant protein, a second operation unit comprising one or a plurality of capture chromatography systems, a third operation unit comprising one or a plurality of post-capture chromatography systems, and a fourth operation unit comprising an ultrafiltration system and diafiltration system.

In some embodiments, the manufacturing system comprises a fifth operation unit located between the first operation unit and the second operation unit, wherein the fifth operation unit comprises a subsystem for preforming virus inactivation. In some embodiments, the manufacturing system comprises a sixth operation unit located between the third operation unit and the fourth operation unit, wherein the sixth operation unit comprises a second subsystem for preforming virus filtration. In some embodiments, the manufacturing system comprises a seventh unit operation comprising a third subsystem, wherein the third subsystem comprises in-line excipients for formulating a therapeutic drug substance.

"Substantially cell-free," as used herein, refers to a sample that is at least or about 90% free (e.g., at least or about 95%, 96%, 97%, 98%, or at least or about 99% free, or about 100% free) of a specified substance such as a mammalian cell.

In particular embodiments, the substantially cell-free sample is removed from a perfusion bioreactor comprising host cells that produce the recombinant protein, a fed-batch bioreactor comprising host cells that produce the recombinant protein, or a clarified liquid culture comprising host cells that produce the recombinant protein.

"Liquid culture medium," as used herein, refers to a fluid that contains sufficient nutrients to allow a cell to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Additional suitable liquid culture mediums are known in the art and are commercially available.

"Perfusion bioreactor," as used herein, refers to a bioreactor containing a plurality of cells in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some embodiments, there is an incremental change (e.g., increase or decrease) in the volume of the first liquid culture medium removed and added over incremental periods (e.g., an about 24-hour period, a period of between about 1 minute and about 24 hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time.

"Fed-batch bioreactor," as used herein, refers to a bioreactor containing a plurality of cells in which necessary nutrients for cell growth and product formation are fed either intermittently or continuously by one or more feed streams.

"Clarified liquid culture medium," as used herein, refers to a liquid culture medium obtained from a bacterial or yeast cell culture that is substantially free (e.g., at least 80%, 85%, 90%, 92%, 94%, 96%, 98%, or 99% free) of bacteria or yeast cells.

"Recombinant protein," as used herein, refers to an immunoglobulin, protein fragment, engineered protein, blood factor, nanobody, or enzyme, including an antibody or antibody fragment therefore.

"Unit operation," as used herein, refers to a functional step that can be performed in a method of manufacturing a recombinant protein, or a component of a system used in a process of manufacturing a recombinant protein. For example, a unit of operation can be filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the recombinant protein, and removing unwanted salts.

The terms "continuous method" or "continuous system," as used herein, refer to a method or system which a fluid is continuously fed through at least a part of the unit operation. A unit operation is continuous if it is capable of processing a continuous flow input for prolonged periods of time. A continuous unit operation has minimal internal hold volume. The output can be continuous or discretized in small packets produced in a cyclic manner. A method is continuous if it is composed of integrated (physically connected) continuous unit operations with zero or minimal hold volume in between.

"Integrated method," as used herein, refers to a method which is performed using structural elements that function cooperatively to achieve a specific result (e.g., the generation of a recombinant protein from a liquid culture medium).

"Eluate," as used herein, refers to a fluid that is emitted from a chromatography column or chromatographic membrane that contains a detectable amount of a recombinant protein.

"Chromatography media," as used herein, refers to the material that is packed into a chromatography column.

In some embodiments, the system disclosed herein is a closed system. A closed system includes unit operations that are designed and operated to limit exposure to the outside environment. Materials may be introduced to a closed system, but the addition must be done in such a way to avoid exposure of the product to the room environment.

The methods and systems disclosed herein comprise capturing a recombinant protein using one or a plurality of capture chromatography systems and eluting the recombinant protein from the one or plurality of capture chromatography systems to produce eluates comprising the recombinant protein. The chromatography media contained in one or more of the capture chromatography systems can be a resin that utilizes a capture mechanism (e.g., Protein A-binding capture mechanism, Protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). In some embodiments, the one or plurality of capture chromatography systems comprise chromatography media consisting of resin beads, porous membranes, or nanofibers. In some embodiments, the chromatography media is functionalized for affinity chromatography, cation exchange chromatography, anion exchange chromatography, hydrophobic interaction chromatography, or mixed-mode chromatography. In some embodiments, the affinity chromatography media is a Protein A-based resin.

In some embodiments, the one or plurality of capture chromatography systems is a periodic counter current chromatography system (PCCS). In some embodiments, the PCCS includes two chromatography columns or includes a modified AKTA system (GE Healthcare, Piscataway, NJ) capable of running up to, for example, four, five, six, seven, eight, or more than eight columns. In some embodiments, the PCCS utilizes a column-switching mechanism. The column-switching events can be triggered by the detection of a level of recombinant protein detected by UV absorbance corresponding to a certain level of recombinant protein in the fluid passing through the chromatography systems, a specific volume of liquid (e.g., buffer), or specific time elapsed.

In order to capture the recombinant protein using capture chromatography systems, one must perform the sequential chromatographic steps of loading, washing, eluting, and regenerating the capture chromatography systems.

In some embodiments, the eluates from the one or plurality of capture chromatography systems are homogenized into a single mixture comprising the recombinant protein. In some embodiments, the homogenized single mixture is subjected to one or a plurality of post-capture chromatography systems and the product output comprising the recombinant protein is collected. The post-capture chromatography systems are used to remove remaining trace or small amounts of contaminants or impurities from a fluid containing a recombinant protein that is close to a final desired purity. In some embodiments, the one or a plurality of post-capture chromatography systems comprises chromatography media consisting of resin beads, porous membranes, or nanofibers. In some embodiments, the chromatography media is functionalized for affinity chromatography, cation exchange chromatography, anion exchange chromatography, hydrophobic interaction chromatography, or mixed-mode chromatography. In some embodiments, the one or plurality of post-capture chromatography columns is a periodic counter current chromatography system (PCCS).

In order to post-capture the recombinant protein using the post-capture chromatography systems, one must perform the sequential chromatographic steps of loading, washing, eluting, and regenerating the post-capture chromatography systems.

In some embodiments, the methods and systems include ultrafiltration (UF) and/or diafiltration (DF) to further purify and concentrate the recombinant protein. UF/DF can increase the concentration of the recombinant protein as well as replace buffering salts with a particular formulation buffer. Ultrafiltration (UF) refers to a type of membrane filtration in which hydrostatic pressure forces a liquid against a semipermeable membrane. In some embodiments, UF is performed with Tangential Flow Filtration (TFF) including single TFF and high performance tangential flow filtration (HPTFF). Single pass tangential flow filtration (SPTFF) refers to any TFF system in which the conversion in a single pass through the module (permeate flow rate divided by inlet feed flow rate) is large enough that the system can be operated without a recycle (recirculation) loop for the retentate. SPTFF can be used for in-line concentration between other unit operations, for example, to reduce process volume prior to a chromatography or precipitation step. Zydney, *Biotechnol. Bioeng.* 113(3): 465-75 (2016).

"Diafiltration," as used herein, refers to a method that uses ultrafiltration membranes to remove, replace, or lower the concentrations of salts or buffering components from solutions containing proteins, such as antibodies, peptides, nucleic acids, and other biomolecules. Continuous diafiltration (also referred to as constant volume diafiltration) involves washing out the original buffer salts (or other low molecular weight species) in the retentate by adding water or a new buffer, such as a formulation buffer, to the retentate to form a formulation containing the recombinantly produced polypeptide. Typically, the new buffer is added at the same rate as filtrate is being generated such that the retentate volume and product concentration does not change appreciably during diafiltration. In particular embodiments, the diafiltration is performed using a single-pass diafiltration cassette.

In some embodiments, the homogenized single mixture is subjected to virus inactivation before being subjected to one or a plurality of post-capture chromatography systems. In some embodiments, the virus inactivation comprises solvent-detergent solution inactivation, heating inactivation, or acidic pH inactivation.

With solvent-detergent viral inactivation, procedures involve subjecting the sample comprising the recombinant protein to an organic solvent and a detergent. The solvent-detergent combination can be any solvent-detergent combination known in the art such as tri-n-butyl phosphate and Triton X100™, Tween 80™ and Sodium cholate and others.

Viral inactivation through heat inactivation involves subjecting the sample comprising the recombinant protein to elevated temperatures. In some embodiments, the methods include heating the sample to a temperature of greater than or equal to 45° C., 46° C., 47° C., 48° C., and up to about greater than or equal to 49° C., 50° C., 51° C., and up. In some embodiments, the sample is heated to a temperature between 45° C. and 65° C.

The period of time during which the sample is heated can vary. For example, in some embodiments, the sample is heated to the target temperature for a time period of between 1 minute and 6 hours. In some embodiments, the sample is heated to the target temperature for a time period of between 10 and 180 minutes, between 20 and 180 minutes, between 20 and 60 minutes, or between 20 and 40 minutes.

In some embodiments, acidic pH inactivation is performed by adjusting the homogenized single mixture to a low pH in-line with one or more solutions and incubating the adjusted homogenized single mixture at the low pH for a period of time that results in a virus inactivation mixture.

The methods and systems disclosed herein include in-line monitoring, including detection of a level of recombinant protein detected by UV absorbance, detection of flow-rate, and/or detection of volume of liquid (e.g., buffer). Monitoring the recombinant protein concentration (e.g., monitoring performed by UV monitoring) can be determined by any tool capable of in-line measurement of product concentration with feedback control.

In some embodiments, the homogenized single mixture is exposed to a low pH for a period of time between 15 minutes to 2 hours. In particular embodiments, the low pH is a pH between 3 and 5. The choice of pH level depends on the stability profile of the recombinant protein and other buffer components. After viral inactivation, the pH of the antibody solution can be adjusted to a more neutral pH, for example, between 4.0 to 8.5 prior to continuing the method.

In some embodiments, viral inactivation is performed in a tubular flow reactor as described by Parker et al., *Biotechnol. Bioeng.* 115(3): 606-16 (2018). In some embodiments, the tubular flow reactor has a defined minimum residence time of at least 30 minutes.

In some embodiments, a virus removal step such as viral filtration is included following collection of the product output from the post-capture chromatography systems. The virus removal step is performed to remove small non-enveloped viruses which are more resistant to the viral inactivation treatment. In some embodiments, the virus filtration is performed in a pressurized loop wherein the pressurized loop comprises a pressure vessel, a virus removal filter, and a sterilizing filter. In some embodiments, the virus removal filter in the pressurized loop is a hollow fiber virus filter. In some embodiments, the pressure vessel is a single-use, closed, and sterilizable vessel. As used herein, the term "sterilizable" refers to a vessel formed from materials that are compatible with known sterilization methods. In some embodiments, the virus filtration is performed using dead-end filtration. As used herein, "dead-end filtration" refers to a filtration where the entire fluid stream being filtered goes through the filter with no recycle or retentate flow. In some embodiments, the virus removal filter is an ultrafilter or a nanofilter. An example of a suitable viral filtration system is disclosed in International Publication No. WO 2018/035116, which is incorporated by reference herein.

In some embodiments, the first unit operation comprises an outlet that is connected to an inlet on the second unit operation, wherein the second unit operation comprises an outlet that is connected to an inlet on the third unit operation, wherein the third unit operation comprises an outlet that is connected to an inlet on the fourth unit operation. In some embodiments, the first unit operation comprises an outlet that is connected to an inlet on the fifth unit operation, wherein the fifth unit operation comprises an outlet that is connected to an inlet on the second unit operation, wherein the second unit operation comprises an outlet that is connected to an inlet on the third unit operation, wherein the third unit operation comprises an outlet that is connected to an inlet on the sixth unit operation, wherein the sixth unit operation comprises an outlet that is connected to an inlet on the fourth unit operation.

In some embodiments, the systems disclosed herein include a surge vessel between each of the first unit operation, the second unit operation, the third unit operation, and the fourth unit operation. The surge vessel is capable of holding any liquid culture before moving into the next operation unit.

The systems described herein can also include a fluid conduit that is disposed between any of the unit operations. Suitable fluid conduits can be a tube that is made of polyethylene, polycarbonate, or plastic. The fluid conduits can also include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; and one or more filters that are disposed in the fluid conduit such that they are capable of filtering (e.g., removing bacteria) the fluid present in the fluid conduit.

In some embodiments, the systems provided herein include a pump system. A pump system can include one or more the following: one or more pumps as known in the art, one or more filters known in the art, and one or more UV detectors.

In some embodiments, following ultrafiltration/diafiltration, one or more excipients are added to the product output to generate a therapeutic drug substance.

"Therapeutic drug substance," as used herein, refers to a substance including a recombinant protein that has been sufficiently purified or isolated from contaminating proteins, lipids, and nucleic acids (e.g., contaminating proteins, lipids, and nucleic acids present in a liquid culture medium or from a host cell (e.g., from a mammalian, yeast, or bacterial host cell) and biological contaminants (e.g., viral and bacterial contaminants), and can be formulated into a pharmaceutical agent without any further substantial purification and/or decontamination step.

In some embodiments, the system disclosed herein is on a skid. "Skid," as used herein, refers to a three-dimensional solid structure that can act as a platform or support for a system described herein. A skid can, if it comprises one or more structures that enable movement (e.g., wheels, rollers, or the like), confer mobility on the system or a portion thereof.

In some embodiments, the methods and systems have a recovery of the recombinant protein of at least about 40%, 50%, 55%, or 60%, and up to about 65%, 70%, 75%, 80%, 85%, 90%, or 95%. In some embodiments, the purification recovery is at least about 60% to about 70%.

In some embodiments, the methods and systems described herein result in a net yield of recombinant protein in the therapeutic protein drug substance of at least about 5 g/day, 10 g/day or 20 g/day, 30 g/day or 40 g/day, and up to about at least about 200 g/day, 300 g/day, 400 g/day, 500 g/day, or 1000 g/day over a continuous period of at least about 5 days, 10 days, 20 days, or 30 days, and up to about at least about 280 days, 290 days, 300 days, 310 days, 320 days, 330 days, 340 days, 350 days, or 365 days.

EXAMPLES

The Examples that follow are illustrative of specific embodiments of the disclosure, and various uses thereof. They are set forth for explanatory purposes only and should not be construed as limiting the scope of the disclosure in any way.

Example 1: Continuous Production of Recombinant Protein

A 100-L intensified perfusion bioreactor coupled with dual ATFs was used to produce a recombinant monoclonal antibody (mAb) over the course of 70 days. The cell-free mAb-containing media (harvest) was continually pumped to a 100-L harvest surge vessel for further processing.

The antibody containing media was captured using 2×1-L (8×20 cm) pre-packed and irradiated Protein A affinity chromatography columns operated in bind-and-elute MCC mode on a pilot scale steam-in-place PCC skid. The capture step was executed such that one of the two columns was always being loaded from the harvest surge vessel and that the average inlet volumetric flowrate to the capture step matched the average outlet volumetric flowrate from the perfusion bioreactor. Loading on the Protein A columns was controlled by Delta UV to approximately 3% breakthrough. Individual capture column eluates were collected in a 5-L mixing vessel prior to viral inactivation. The Protein A operation was integrated with the perfusion bioreactor on day 12 and ran continuously for 58 days. Data summarizing Protein A operation performance are shown in FIGS. 3A-3F.

The individual Protein A eluates were mixed in the 5-L mixing vessel to ensure a homogeneous stream for the virus inactivation unit operation. The outflow of the mixing vessel was automated such that the entire vessel would be processed before the next Protein A elution cycle. The homogenized Protein A eluate was adjusted in-line by addition of 1 M acetic acid to a target pH of 3.6. The low pH adjusted Protein A eluate was then pumped through a tubular flow reactor (TFR) with a defined minimum residence time of ≥30 minutes to ensure sufficient time at low pH to achieve complete viral inactivation. The virus inactivated Protein A eluate was then adjusted in-line by addition of 0.75 M sodium acetate to a target pH of 4.5. The adjusted virus inactivated Protein A eluate was then processed through a sterilizing grade filter and continuously collected in a small surge vessel for further processing. The virus inactivation operation was integrated with the preceding operations on day 15, and ran continuously for 55 days. Data summarizing viral inactivation operation performance are shown in FIGS. 4A-4G.

The adjusted virus inactivated Protein A eluate was further processed through two orthogonal chromatography operations using mixed-mode anion exchange resin and hydrophobic interaction chromatography resin, operated in flow-through mode. For this example process, there was no interstep adjustment between the two post-capture chromatography operations, allowing the flowthrough from the mixed-mode column to be directly loaded on to the hydrophobic interaction column. The post capture train consisted of 2×0.2 L (5×10 cm) pre-packed mixed-mode columns and 2×0.2 L (5×10 cm) pre-packed hydrophobic interaction columns, operated in MCC mode on the same PCC skid as the Protein A operation. The adjusted and virus inactivated Protein A eluate stream was continuously loaded on one of the two parallel post-capture trains with column loading automated such that mass equivalent to approximately 2 Protein A eluates was loaded in each post-capture cycle.

The combined mixed-mode/hydrophobic interaction flowthrough (labeled as post capture eluate) was continuously collected in a small surge vessel for further processing. The post-capture chromatography operation was integrated with the preceding unit operations on Day 23, and ran continuously for 47 days. Data summarizing the post-capture chromatography operation performance are shown in FIGS. 5A-5D.

Figure 6A:
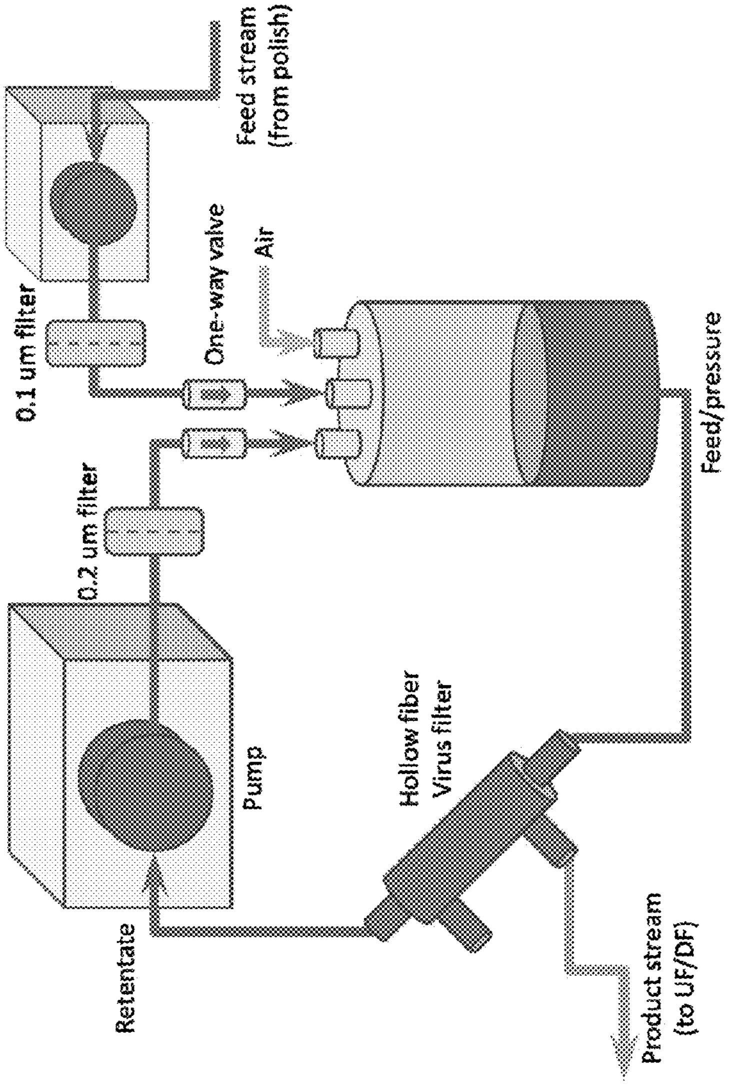
FIG. 6A shows a schematic of the virus filtration for the methods and systems disclosed herein.
Figure 6B:
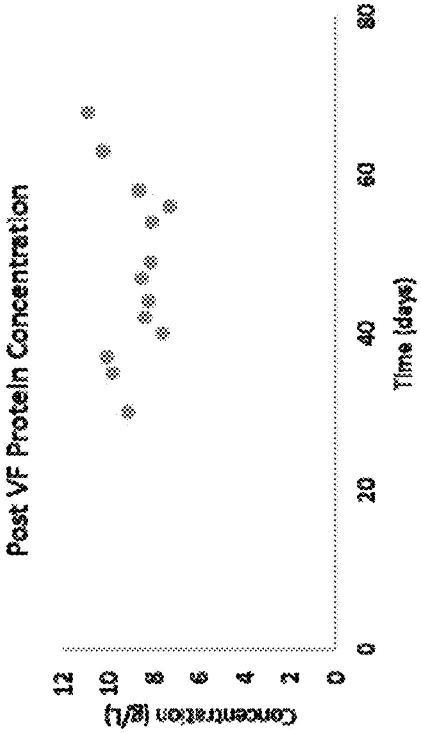
FIGS. 6B-6G are graphs showing viral filtration operation performance for the methods and systems disclosed herein.
Figure 6C:
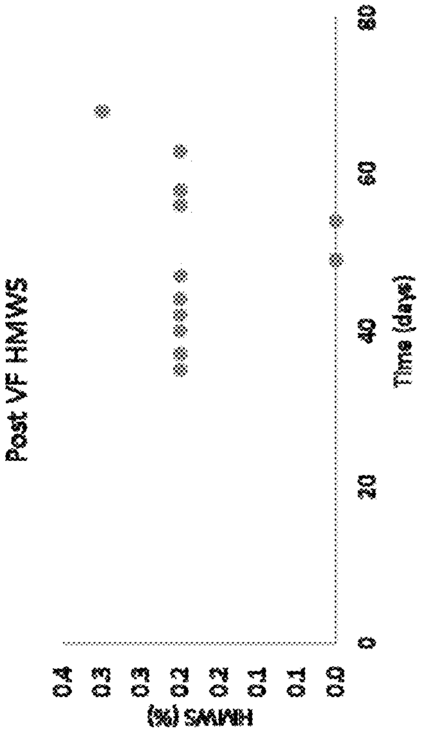
Figure 6D:
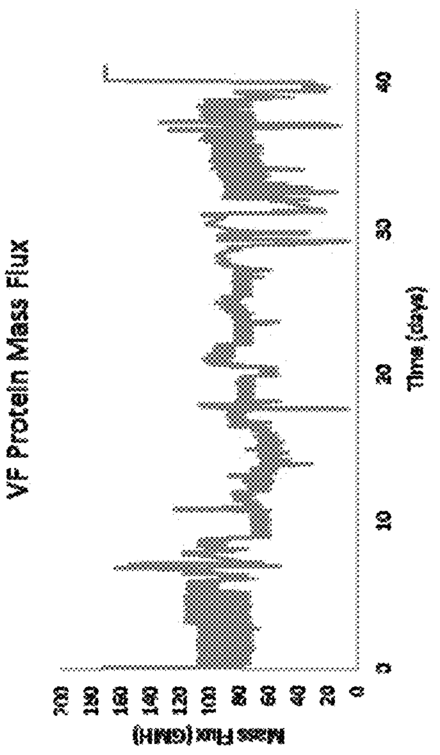
Figure 6E:
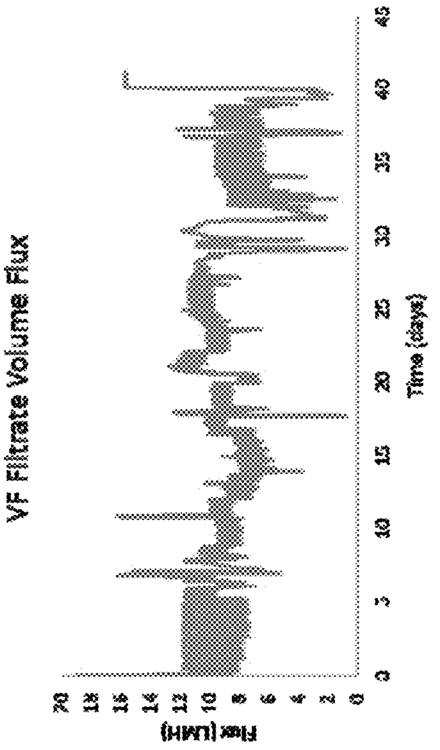
Figure 6G:
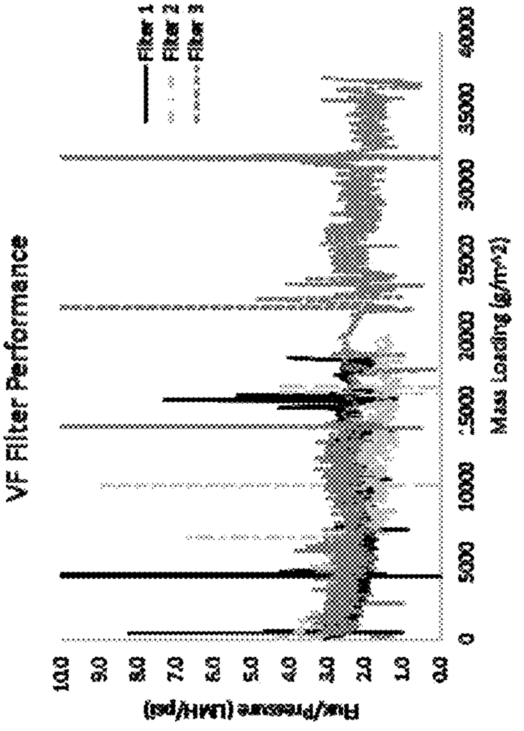
Figure 6F:
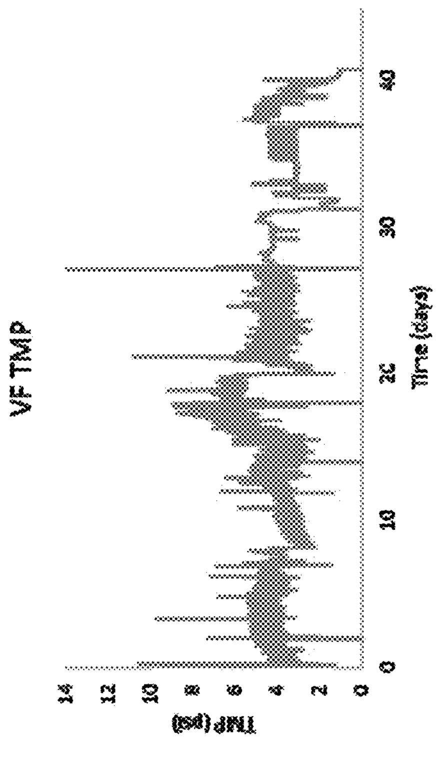
Figure 7B:
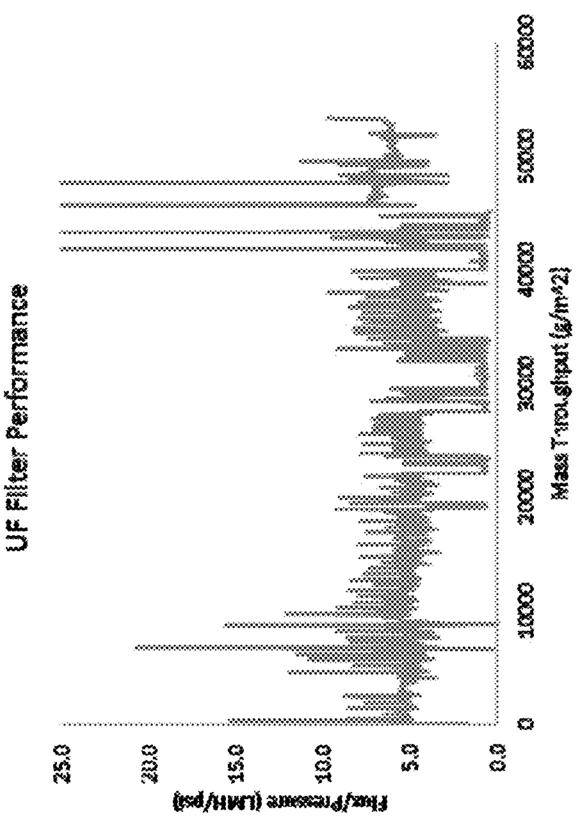
FIGS. 7A-7E are graphs showing ultrafiltration operation performance for the methods and systems disclosed herein.
Figure 7A:
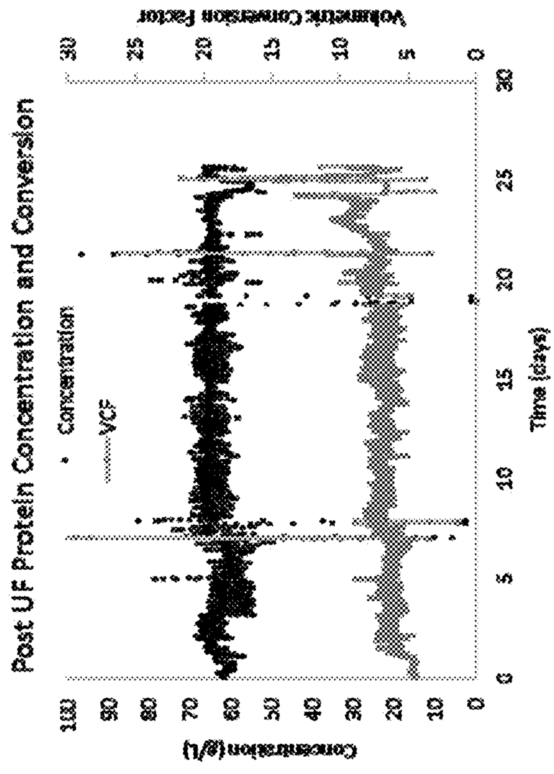
Figure 7C:
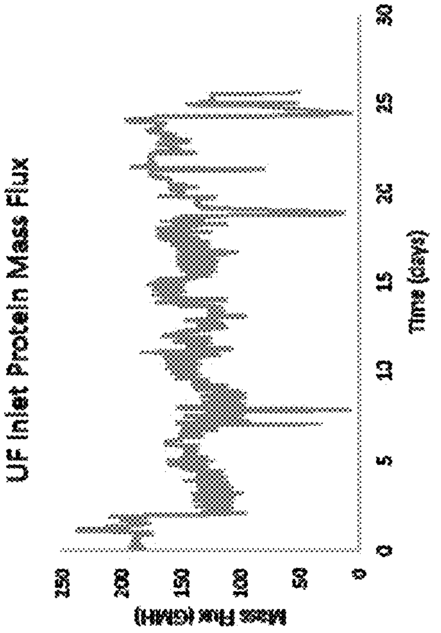
Figure 7D:
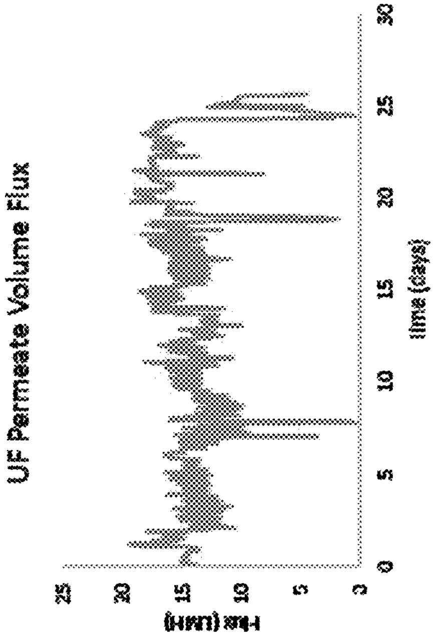
Figure 7E:
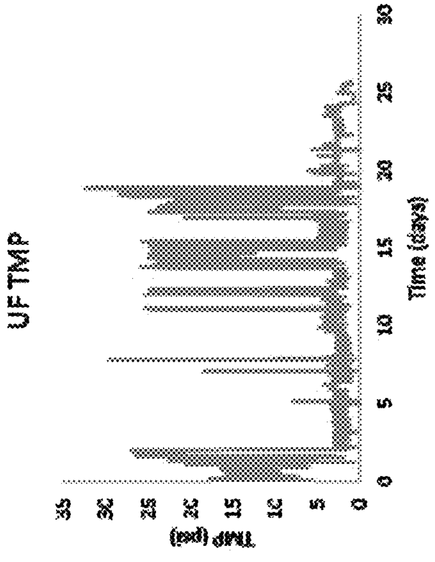
Figure 8A:
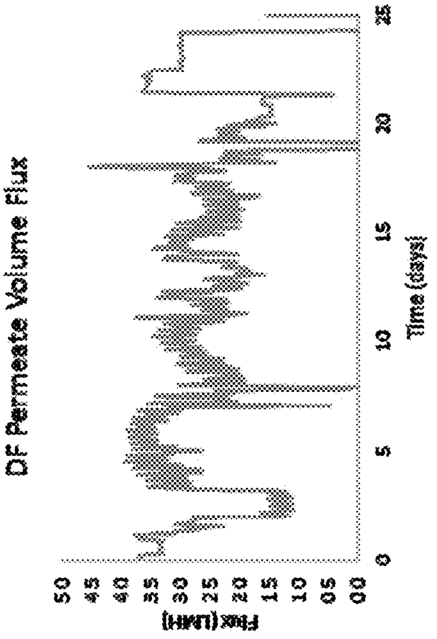
FIGS. 8A-8E are graphs showing diafiltration operation performance for the methods and systems disclosed herein.
Figure 8B:
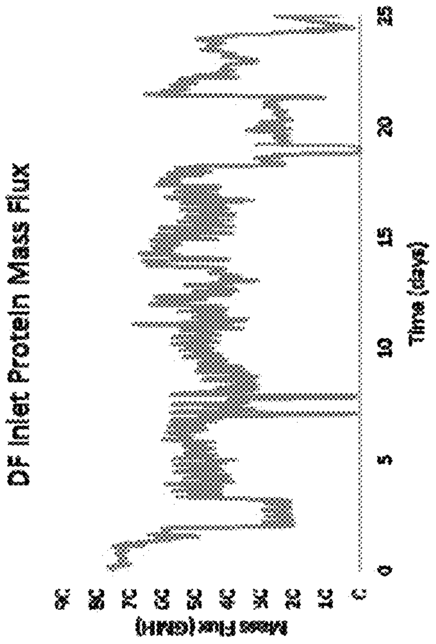
Figure 8C:
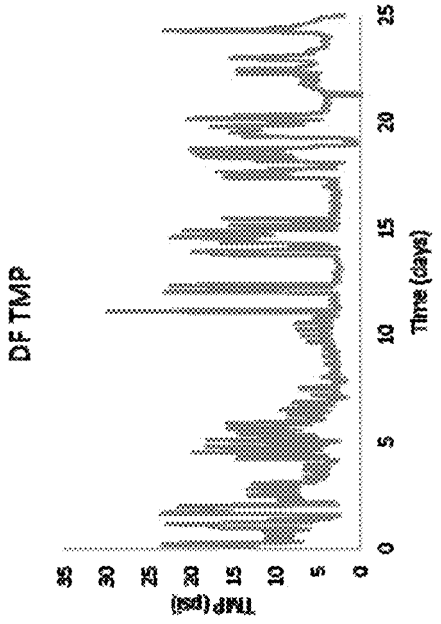
Figure 8D:
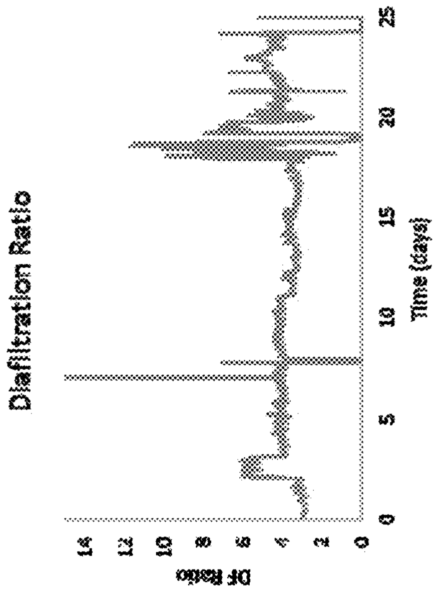
Figure 8E:
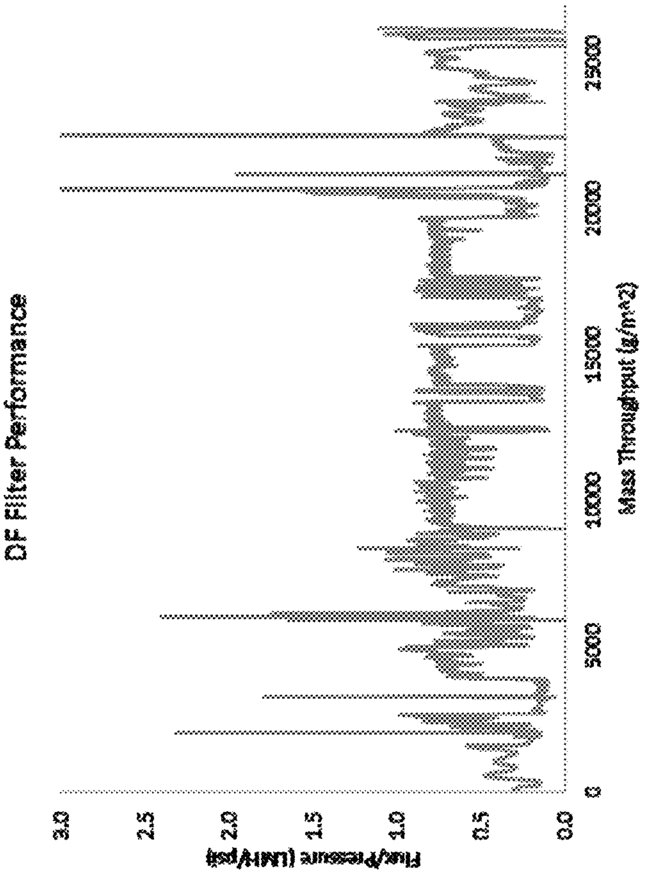
Figure 9A:
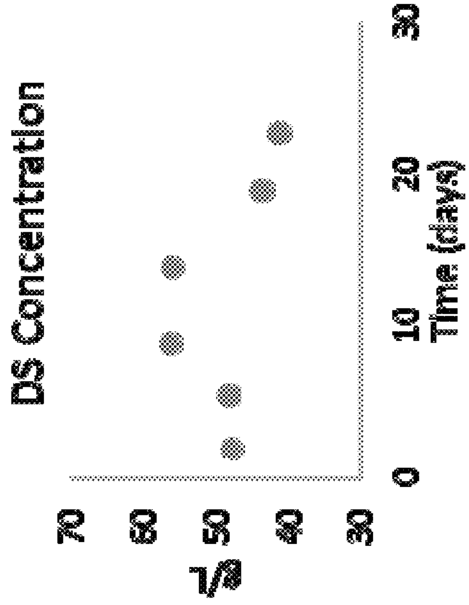
FIGS. 9A-9H are graphs showing attributes for a drug substance produced using the methods and systems disclosed herein.
Figure 9B:
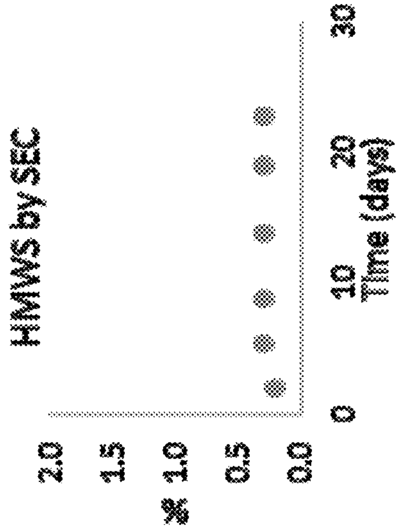
Figure 9D:
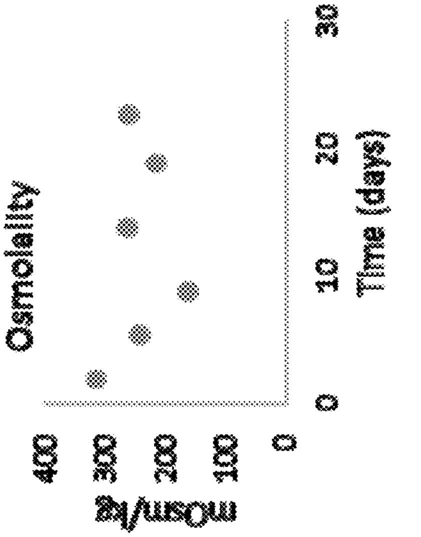
Figure 9C:
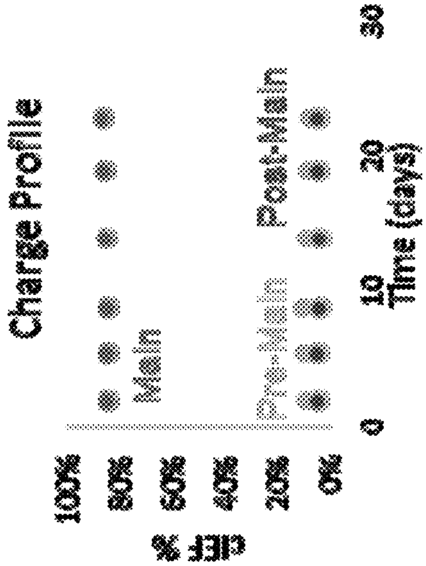
Figure 9E:
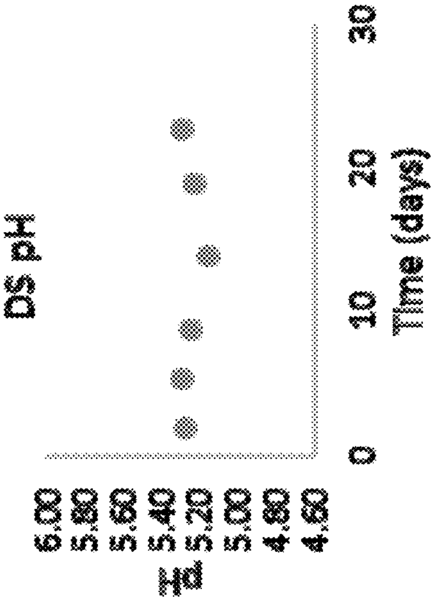
Figure 9F:
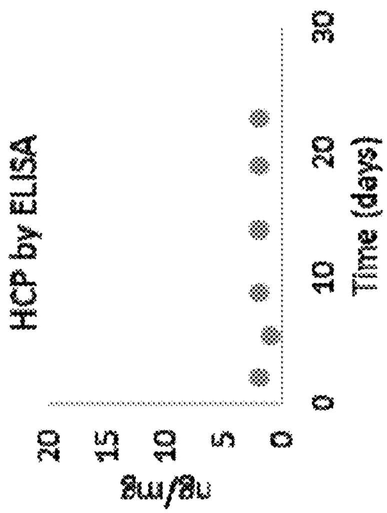
Figure 9G:
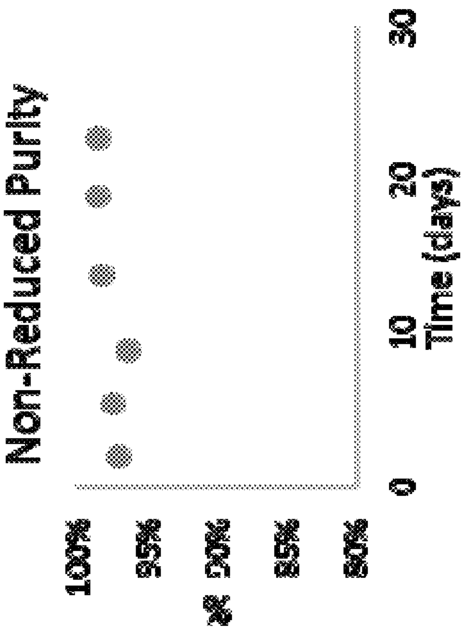
Figure 9H:
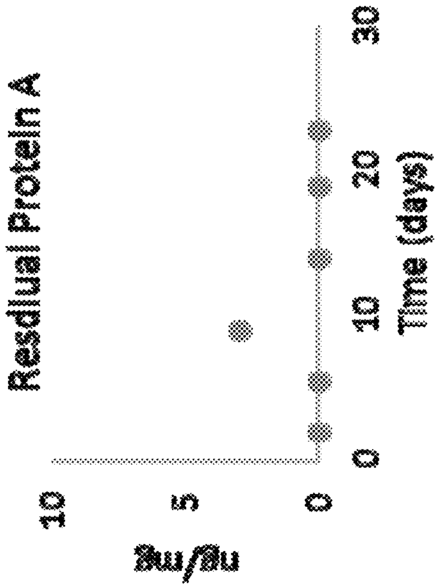

The post-capture eluates were further processed through a 0.1 $m^2$ Planova 20N (AK Bio) virus removal filter operated in tangential flow mode. Post-capture eluate was continuously transferred from the surge vessel to a pressurized loop containing a pressure vessel, the virus removal filter, a sterilizing grade filter, and a peristaltic pump to drive the recirculation, as shown in FIG. 6A. The pressure in the loop was automated so the net volumetric flowrate through the virus filter (permeate flux) was equal to the net volumetric flowrate out from the post-capture operation. The Planova 20N filter was periodically replaced based on preliminary virus validation studies. The virus filtered material was continuously collected in a small surge vessel for further processing. The virus filtration operation was integrated with the preceding unit operations on Day 29, and ran continuously for 41 days. Data summarizing viral filtration operation performance are shown in FIGS. 6B-6F.

The virus filtered material was further processed via ultrafiltration using a 0.065 $m^2$ ILC single-pass TFF (SP-TFF) cassette and concentrated to a target mAb concentration of 65 g/L. Material was pumped from the post virus filtration surge vessel to the inlet of the SP-TFF cassette at a volumetric flowrate that matched the outlet flowrate from the virus filtration operation. The retentate flowrate from the SP-TFF cassette was automatically controlled using a feedback loop via an in-line measurement of the product concentration to maintain the target concentration value. The concentrated mAb stream was then pumped directly to the inlet of a single-pass diafiltration (SP-DF) cassette to perform in-line buffer exchange. Diafiltration buffer was pumped to the buffer inlet of the SP-DF cassette and buffer flow was automated to maintain a constant ratio of buffer to product flow. The retentate flowrate was controlled to match the inlet flowrate. The buffer exchanged DF retentate stream was then formulated by the in-line addition of a concentrated excipient solution to generate formulated bulk. The formulated bulk was further processed through a sterilizing grade filter to generate drug substance, which was collected in a single-use vessel. The ultrafiltration and diafiltration operations were integrated with the preceding unit operations on Day 42, and ran continuously for 29 days. The formulation operation and drug substance generation was integrated on Day 46, and ran continuously for 25 days. Over the course of 25 days, 6 batches of drug substance were generated. Data summarizing ultrafiltration and diafiltration operation performance are shown in FIGS. 7A-7E and FIGS. 8A-8D. FIGS. 9A-9H show attributes for the generated drug substance.

Example 2: Continuous Production of Recombinant Protein

A 100-L intensified perfusion bioreactor coupled with dual ATFs was used to produce a recombinant monoclonal antibody (mAb) over the course of 27 days. The cell-free mAb-containing media (harvest) was continually pumped to a 100-L harvest surge vessel for further processing.

The antibody containing media was captured using 2×1-L (8×20 cm) pre-packed and irradiated Protein A affinity chromatography columns operated in bind-and-elute MCC mode on a pilot scale steam-in-place PCC skid. The capture step was executed such that one of the two columns was always being loaded from the harvest surge vessel and that the average inlet volumetric flowrate to the capture step matched the average outlet volumetric flowrate from the perfusion bioreactor. Loading on the Protein A columns was controlled by Delta UV to approximately 3% breakthrough. Individual capture column eluates were collected in a 5-L mixing vessel prior to viral inactivation. The Protein A operation was integrated with the perfusion bioreactor on day 12 and ran continuously for 15 days.

The individual Protein A eluates were mixed in the 5-L mixing vessel to ensure a homogeneous stream for the virus inactivation unit operation. The outflow of the mixing vessel was automated such that the entire vessel would be processed before the next Protein A elution cycle. The homogenized Protein A eluate was adjusted in-line by addition of 1 M acetic acid to a target pH of 3.6. The low pH adjusted Protein A eluate was then pumped through a 3D-printed, gamma irradiated tubular flow reactor (TFR) with a defined minimum residence time of ≥30 minutes to ensure sufficient time at low pH to achieve complete viral inactivation. The virus inactivated Protein A eluate was then adjusted in-line by addition of 0.75 M sodium acetate to a target pH of 4.5. The adjusted virus inactivated Protein A eluate was then processed through a sterilizing grade filter and continuously collected in a small surge vessel for further processing. The virus inactivation operation was integrated with the preceding operations on day 13, and ran continuously for 14 days.

The adjusted virus inactivated Protein A eluate was further processed through two orthogonal chromatography operations using mixed-mode anion exchange resin and hydrophobic interaction chromatography resin, operated in flow-through mode. The post capture train consisted of 2×0.2 L (5×10 cm) pre-packed and gamma-irradiated mixed-mode columns and 2×0.2 L (5×10 cm) pre-packed and gamma-irradiated hydrophobic interaction columns, operated in MCC mode. The adjusted and virus inactivated Protein A eluate stream was continuously loaded on one of the two mixed-mode columns and the flowthrough of the mixed-mode column was continuously loaded on one of the two hydrophobic interaction columns. The mixed-mode and hydrophobic interaction columns were independently loaded to their respective loading capacities.

The post-capture chromatography operation was integrated with the preceding unit operations on Day 14, and ran continuously for 13 days.

The post-capture eluates were further processed through a 0.1 $m^2$ Planova 20N (AK Bio) virus removal filter operated in tangential flow mode. Post-capture eluate was continuously transferred from the outlet of the hydrophobic interaction column to a pressurized loop containing a pressure vessel, the virus removal filter, a sterilizing grade filter, and a peristaltic pump to drive the recirculation. The pressure in the loop was automated so the net volumetric flowrate through the virus filter (permeate flux) was equal to the net volumetric flowrate out from the post-capture operation. The virus filtered material was continuously collected in a small surge vessel for further processing. The virus filtration operation was integrated with the preceding unit operations on Day 14, and ran continuously for 13 days.

The virus filtered material was further processed via ultrafiltration using 2×0.1 $m^2$ gamma-irradiated TFF capsules in series, operated in single-pass mode. The virus filtered material was concentrated to a target mAb concentration of 110 g/L. Material was pumped from the post virus filtration surge vessel to the inlet of the TFF capsule at a volumetric flowrate that matched the outlet flowrate from the virus filtration operation. The retentate flowrate from the TFF capsule was automatically controlled using a feedback loop via an in-line measurement of the product concentration to maintain the target concentration value. The concentrated mAb stream was then pumped directly to the inlet of a gamma-irradiated single-pass diafiltration (SP-DF) cassette to perform in-line buffer exchange. Diafiltration buffer was pumped to the buffer inlet of the SP-DF cassette and buffer flow was automated to maintain a constant ratio of buffer to product flow. The retentate flowrate was controlled to match the inlet flowrate. The buffer exchanged DF retentate stream was then formulated by the in-line addition of a concentrated excipient solution to generate formulated bulk. The addition of the formulation buffer was controlled via a feedback loop and an in-line sensor measuring the level of excipients in the formulated stream. The formulated bulk was further processed through a sterilizing grade filter to generate drug substance, which was collected in a single-use vessel. The ultrafiltration and diafiltration operation was integrated with the proceeding unit operations on Day 18 and the formulation operation was integrated on Day 20.

Due to issues with the in-line sensors, the UF/DF and formulation operations did not achieve steady state prior to the end of the campaign.

While the disclosure has been described in terms of various embodiments, it is understood that variations and modifications will occur to those skilled in the art. Therefore, it is intended that the appended claims cover all such equivalent variations that come within the scope of the disclosure as claimed. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

What is claimed is:

1. A manufacturing system for producing a recombinant protein, the manufacturing system comprising:

(a) a first unit operation subsystem comprising a bioreactor comprising host cells that produce the recombinant protein;

(b) a second unit operation subsystem comprising one or a plurality of capture chromatography systems;

(c) a third unit operation subsystem comprising one or a plurality of post-capture chromatography systems; and (d) a fourth unit operation subsystem comprising an ultrafiltration system and diafiltration system;

wherein each unit operation subsystem is physically connected from the first unit operation subsystem to the fourth unit operation subsystem, and wherein the connected unit operation subsystems are configured to perform a continuous flow process comprising flowing the recombinant protein from the first unit operation subsystem to the fourth unit operation subsystem continuously; and wherein the ultrafiltration system is configured to perform single-pass tangential flow filtration and the diafiltration system is configured to perform single-pass diafiltration, and wherein the diafiltration system is configured to perform in-line buffer exchange.

2. The manufacturing system of claim 1, further comprising a fifth unit operation subsystem located between the first unit operation subsystem and the second unit operation subsystem, wherein the fifth unit operation subsystem is configured to perform virus inactivation.

3. The manufacturing system of claim 2, wherein the fifth unit operation subsystem comprises a tubular flow reactor.

4. The manufacturing system of claim 1 further comprising a sixth unit operation subsystem located between the third unit operation subsystem and the fourth unit operation subsystem, wherein the sixth unit operation subsystem is configured to perform virus filtration.

5. The manufacturing system of claim 1, wherein the one or plurality of capture chromatography systems and the one or a plurality of post-capture chromatography systems comprises chromatography media comprising resin beads, porous membranes, or nanofibers.

6. The manufacturing system of claim 5, wherein the chromatography media is functionalized for affinity chromatography, cation exchange chromatography, anion exchange chromatography, hydrophobic interaction chromatography, or mixed-mode chromatography.

7. The manufacturing system of claim 5, wherein the chromatography media is functionalized for affinity chromatography.

8. The manufacturing system of claim 1, wherein the one or plurality of capture chromatography systems and the one or a plurality of post-capture chromatography systems are each a periodic counter current chromatography system (PCCS).

9. The manufacturing system of claim 3, wherein the tubular flow reactor has a defined minimum residence time of at least 30 minutes.

10. The manufacturing system of claim 4, wherein the sixth unit operation subsystem configured to perform virus filtration comprises a pressurized container comprising a virus removal filter and a sterilizing filter.

11. The manufacturing system of claim 10, wherein the pressurized container is a single-use, closed, and sterilizable container.

12. The manufacturing system of claim 10, wherein the virus removal filter is an ultrafilter or a nanofilter.

13. The manufacturing system of claim 1, wherein the first unit operation subsystem comprises an outlet that is connected to an inlet on the second unit operation subsystem, wherein the second unit operation subsystem comprises an outlet that is connected to an inlet on the third unit operation subsystem, wherein the third unit operation subsystem comprises an outlet that is connected to an inlet on the fourth unit operation subsystem.

14. The manufacturing system of claim 1 further comprising a surge vessel between each of the first unit operation subsystem, the second unit operation subsystem, the third unit operation subsystem, and the fourth unit operation subsystem.

15. The manufacturing system of claim 1, wherein the recombinant protein is an antibody or antigen-binding fragment thereof.

16. The manufacturing system of claim 1, wherein the manufacturing system is on a skid.

17. The manufacturing system of claim 1, wherein the manufacturing system is closed.

18. The manufacturing system of claim 1 further comprising a seventh unit operation subsystem configured to formulate a therapeutic drug substance via in-line addition of excipients.

19. The manufacturing system of claim 1, wherein the ultrafiltration system is configured to perform single-pass tangential flow filtration in a single-pass tangential flow cassette.

20. The manufacturing system of claim 1, wherein the diafiltration system is configured to perform single-pass diafiltration in a single-pass diafiltration cassette.

21. The manufacturing system of claim 1, wherein the ultrafiltration system comprises a single-pass tangential flow cassette.

22. The manufacturing system of claim 1, wherein the diafiltration system comprises a single-pass diafiltration cassette.

23. The manufacturing system of claim 7, wherein the chromatography media functionalized for affinity chromatography is a Protein A based resin.

* * * * *